(12) United States Patent
Davis

(10) Patent No.: US 12,296,112 B2
(45) Date of Patent: May 13, 2025

(54) MICROFABRICATED CATHETER DEVICES WITH HIGH AXIAL STRENGTH

(71) Applicant: SCIENTIA VASCULAR, Inc., West Valley City, UT (US)

(72) Inventor: Clark C. Davis, Holladay, UT (US)

(73) Assignee: Scientia Vascular, Inc., West Valley, UT (US)

( * ) Notice: Subject to any disclaimer, the term of this patent is extended or adjusted under 35 U.S.C. 154(b) by 71 days.

(21) Appl. No.: 17/493,265

(22) Filed: Oct. 4, 2021

(65) Prior Publication Data

US 2022/0105312 A1 Apr. 7, 2022

Related U.S. Application Data

(60) Provisional application No. 63/087,410, filed on Oct. 5, 2020.

(51) Int. Cl.
*A61M 25/00* (2006.01)
*A61M 25/09* (2006.01)
(Continued)

(52) U.S. Cl.
CPC .... *A61M 25/0045* (2013.01); *A61M 25/0053* (2013.01); *A61M 25/001* (2013.01);
(Continued)

(58) Field of Classification Search
CPC .......... A61M 25/0045; A61M 25/0053; A61M 25/001; A61M 25/0013; A61M 25/0021;
(Continued)

(56) References Cited

U.S. PATENT DOCUMENTS 2,022,065 A 11/1935 Wappler
2,187,299 A 1/1940 Otto
(Continued)

FOREIGN PATENT DOCUMENTS

AU 07230/40 B2 8/2000
AU 733966 B2 5/2001
(Continued)

OTHER PUBLICATIONS

International Search Report and Written Opinion received for PCT Patent Application No. PCT/US2021/053647, mailed on Dec. 28, 2021, 9 pages.
(Continued)

*Primary Examiner* — Nathan R Price
*Assistant Examiner* — Haden Matthew Ritchie
(74) *Attorney, Agent, or Firm* — Workman Nydegger

(57) ABSTRACT

This disclosure describes microfabricated intravascular devices that are configured for high axial strength while also maintaining effective bending flexibility. A tube member includes a series of circumferentially extending rings connected to one another by a series of axially extending beams. Transverse cuts separate and define the rings. A series of axial cuts are aligned with the beams and extend from the beams partially into the adjoining rings so that the beam length is nested partially within the axial length of the adjoining rings. This increases the functional length of the beams to provide bending flexibility while still sufficient ring structure to provide effective axial stiffness.

19 Claims, 4 Drawing Sheets

(51) Int. Cl.
*A61M 25/10* (2013.01)
*A61M 25/01* (2006.01)

(52) U.S. Cl.
CPC ..... *A61M 25/0013* (2013.01); *A61M 25/0021* (2013.01); *A61M 25/0023* (2013.01); *A61M 25/0026* (2013.01); *A61M 2025/0042* (2013.01); *A61M 25/005* (2013.01); *A61M 25/0054* (2013.01); *A61M 25/0108* (2013.01); *A61M 25/0138* (2013.01); *A61M 25/0147* (2013.01); *A61M 25/09* (2013.01); *A61M 2025/09108* (2013.01); *A61M 2025/0915* (2013.01); *A61M 25/104* (2013.01)

(58) Field of Classification Search
CPC .......... A61M 25/0023; A61M 25/0026; A61M 25/005; A61M 25/0054; A61M 25/0108; A61M 25/0138; A61M 25/0147; A61M 25/09; A61M 25/104; A61M 25/0051; A61M 2025/0042; A61M 2025/09108; A61M 2025/0915
See application file for complete search history.

(56) References Cited

U.S. PATENT DOCUMENTS

| | | | |
|---|---|---|---|
| 3,183,702 A | 5/1965 | Zittell |
| 3,572,334 A | 3/1971 | Petterson |
| 3,612,058 A | 10/1971 | Ackerman |
| 3,709,271 A | 1/1973 | Flory |
| 3,782,233 A | 1/1974 | Helm |
| 3,920,058 A | 11/1975 | Walker |
| 4,163,406 A | 8/1979 | Crawford |
| 4,239,069 A | 12/1980 | Zimmerman |
| 4,416,312 A | 11/1983 | Ostberg |
| 4,688,540 A | 8/1987 | Ono |
| 4,719,924 A | 1/1988 | Crittenden et al. |
| 4,801,297 A | 1/1989 | Mueller |
| 4,846,186 A | 7/1989 | Box et al. |
| 4,895,168 A | 1/1990 | Machek |
| 4,989,608 A | 2/1991 | Ratner |
| 5,047,045 A | 9/1991 | Arney et al. |
| 5,069,217 A | 12/1991 | Fleischhacker, Jr. |
| 5,084,022 A | 1/1992 | Claude |
| 5,095,915 A | 3/1992 | Engelson |
| 5,102,390 A | 4/1992 | Crittenden et al. |
| 5,144,959 A | 9/1992 | Gambale et al. |
| 5,147,317 A | 9/1992 | Shank et al. |
| 5,154,725 A | 10/1992 | Leopold |
| 5,174,302 A | 12/1992 | Palmer |
| 5,315,996 A | 5/1994 | Lundquist |
| 5,326,374 A | 7/1994 | Ilbawi et al. |
| 5,345,945 A | 9/1994 | Hodgson et al. |
| 5,372,587 A | 12/1994 | Hammerslag et al. |
| 5,381,782 A * | 1/1995 | DeLaRama ......... A61B 1/0056 604/95.01 |
| 5,382,259 A | 1/1995 | Phelps et al. |
| 5,385,152 A | 1/1995 | Abele et al. |
| 5,437,288 A | 8/1995 | Schwartz et al. |
| 5,441,483 A | 8/1995 | Avitall |
| D363,544 S | 10/1995 | Rowland et al. |
| D363,776 S | 10/1995 | Rowland et al. |
| 5,480,382 A | 1/1996 | Hammerslag et al. |
| 5,506,682 A | 4/1996 | Pryor |
| 5,507,751 A | 4/1996 | Goode et al. |
| 5,551,444 A | 9/1996 | Finlayson |
| 5,554,114 A | 9/1996 | Wallace et al. |
| 5,569,218 A | 10/1996 | Berg |
| 5,573,520 A | 11/1996 | Schwartz et al. |
| 5,573,867 A | 11/1996 | Zafred et al. |
| 5,606,981 A | 3/1997 | Tartacower et al. |
| 5,659,205 A | 8/1997 | Weisser |
| 5,673,707 A | 10/1997 | Chandrasekaran |
| 5,676,659 A | 10/1997 | McGurk |
| 5,685,568 A | 11/1997 | Pirrello |
| 5,685,868 A | 11/1997 | Lundquist |
| 5,690,120 A | 11/1997 | Jacobsen et al. |
| 5,706,826 A | 1/1998 | Schwager |
| 5,741,429 A | 4/1998 | Donadio et al. |
| 5,746,701 A | 5/1998 | Noone |
| 5,792,154 A | 8/1998 | Doan et al. |
| 5,797,857 A | 8/1998 | Obitsu |
| 5,800,454 A | 9/1998 | Jacobsen et al. |
| 5,833,631 A | 11/1998 | Nguyen |
| 5,833,632 A | 11/1998 | Jacobsen et al. |
| 5,842,461 A | 12/1998 | Azuma |
| 5,860,963 A | 1/1999 | Azam et al. |
| 5,876,356 A | 3/1999 | Viera et al. |
| 5,911,715 A | 6/1999 | Berg et al. |
| 5,911,717 A | 6/1999 | Jacobsen et al. |
| 5,916,194 A | 6/1999 | Jacobsen et al. |
| 5,931,830 A | 8/1999 | Jacobsen et al. |
| 5,954,672 A | 9/1999 | Schwager |
| 6,004,279 A | 12/1999 | Crowley et al. |
| 6,014,919 A | 1/2000 | Jacobsen |
| 6,017,319 A | 1/2000 | Jacobsen et al. |
| 6,022,343 A | 2/2000 | Johnson et al. |
| 6,022,369 A | 2/2000 | Jacobsen et al. |
| 6,027,863 A | 2/2000 | Donadio, III |
| 6,033,288 A | 3/2000 | Weisshaus et al. |
| 6,033,394 A | 3/2000 | Vidlund et al. |
| 6,056,702 A | 5/2000 | Lorenzo |
| 6,063,101 A | 5/2000 | Jacobsen et al. |
| 6,110,164 A | 8/2000 | Vidlund |
| 6,132,389 A | 10/2000 | Cornish et al. |
| 6,139,511 A | 10/2000 | Huter et al. |
| D435,909 S | 1/2001 | Ogino et al. |
| 6,168,570 B1 | 1/2001 | Ferrera |
| 6,179,828 B1 | 1/2001 | Mottola et al. |
| 6,183,410 B1 | 2/2001 | Jacobsen et al. |
| 6,183,420 B1 | 2/2001 | Douk et al. |
| 6,214,042 B1 | 4/2001 | Jacobsen et al. |
| 6,228,073 B1 | 5/2001 | Noone et al. |
| 6,245,030 B1 | 6/2001 | Dubois et al. |
| 6,251,086 B1 | 6/2001 | Cornelius et al. |
| 6,260,458 B1 | 7/2001 | Jacobsen et al. |
| 6,261,246 B1 | 7/2001 | Pantages et al. |
| 6,273,881 B1 | 8/2001 | Kiemeneij |
| 6,302,870 B1 | 10/2001 | Jacobsen et al. |
| 6,306,105 B1 | 10/2001 | Rooney et al. |
| 6,346,091 B1 | 2/2002 | Jacobsen et al. |
| 6,356,791 B1 | 3/2002 | Westlund et al. |
| 6,402,706 B2 | 6/2002 | Richardson et al. |
| 6,428,489 B1 | 8/2002 | Jacobsen et al. |
| 6,431,039 B1 | 8/2002 | Jacobsen et al. |
| 6,436,056 B1 | 8/2002 | Wang et al. |
| 6,440,088 B1 | 8/2002 | Jacobsen et al. |
| 6,458,867 B1 | 10/2002 | Wang et al. |
| 6,464,651 B1 | 10/2002 | Hiejima et al. |
| 6,492,615 B1 | 12/2002 | Flanagan |
| 6,494,894 B2 | 12/2002 | Mirarchi |
| 6,527,732 B1 | 3/2003 | Strauss et al. |
| 6,527,746 B1 | 3/2003 | Oslund et al. |
| 6,553,880 B2 | 4/2003 | Jacobsen et al. |
| 6,554,820 B1 | 4/2003 | Wendlandt et al. |
| 6,558,355 B1 | 5/2003 | Metzger et al. |
| 6,579,246 B2 | 6/2003 | Jacobsen et al. |
| 6,602,207 B1 | 8/2003 | Mam et al. |
| 6,606,985 B2 | 8/2003 | Negishi |
| 6,610,046 B1 | 8/2003 | Usami et al. |
| 6,627,724 B2 | 9/2003 | Meijs et al. |
| 6,652,508 B2 | 11/2003 | Griffin et al. |
| 6,671,560 B2 | 12/2003 | Westlund et al. |
| 6,766,720 B1 | 7/2004 | Jacobsen et al. |
| 6,805,676 B2 | 10/2004 | Klint |
| 6,866,642 B2 | 3/2005 | Kellerman et al. |
| RE39,018 E | 3/2006 | Azuma et al. |
| 7,024,885 B2 | 4/2006 | Rold |
| 7,097,624 B2 | 8/2006 | Campion et al. |
| 7,110,910 B1 | 9/2006 | Deffenbaugh et al. |
| 7,128,718 B2 | 10/2006 | Hojeibane et al. |
| 7,172,587 B2 | 2/2007 | Poole et al. |
| 7,182,735 B2 | 2/2007 | Shireman et al. |

(56) References Cited

U.S. PATENT DOCUMENTS

| | | | |
|---|---|---|---|
| 7,276,062 B2 | 10/2007 | McDaniel et al. |
| 7,338,345 B2 | 3/2008 | Fujinami |
| 7,421,929 B2 | 9/2008 | French |
| 7,494,474 B2 | 2/2009 | Richardson et al. |
| 7,507,246 B2 | 3/2009 | McGuckin et al. |
| D598,094 S | 8/2009 | Alber |
| 7,621,880 B2 | 11/2009 | Ryan et al. |
| 7,637,875 B2 | 12/2009 | Yutaka |
| 7,641,622 B2 | 1/2010 | Satou et al. |
| D611,596 S | 3/2010 | Kousai et al. |
| 7,670,302 B2 | 3/2010 | Griffin et al. |
| 7,699,792 B2 | 4/2010 | Hofmann et al. |
| 7,722,545 B2 | 5/2010 | Bertsch |
| 7,722,552 B2 | 5/2010 | Aimi et al. |
| 7,744,545 B2 | 6/2010 | Aimi et al. |
| 7,747,314 B2 | 6/2010 | Parins et al. |
| 7,753,859 B2 | 7/2010 | Kinoshita et al. |
| 7,766,896 B2 | 8/2010 | Kornkven et al. |
| 7,769,839 B2 | 8/2010 | Boivie et al. |
| 7,785,273 B2 | 8/2010 | Eskuri |
| 7,789,839 B2 | 9/2010 | Lupton |
| 7,806,837 B2 | 10/2010 | Rasmussen et al. |
| 7,878,984 B2 | 2/2011 | Jacobsen et al. |
| 7,883,474 B1 | 2/2011 | Mirigian et al. |
| 7,914,467 B2 | 3/2011 | Layman et al. |
| 7,942,832 B2 | 5/2011 | Kanuka et al. |
| 7,989,042 B2 | 8/2011 | Obara et al. |
| 8,007,434 B2 | 8/2011 | Olson |
| 8,043,314 B2 | 10/2011 | Noriega et al. |
| 8,048,004 B2 | 11/2011 | Davis et al. |
| 8,092,444 B2 | 1/2012 | Lentz et al. |
| 8,105,246 B2 | 1/2012 | Voeller et al. |
| 8,128,579 B2 | 3/2012 | Chen et al. |
| 8,128,580 B2 | 3/2012 | Fujimagari et al. |
| 8,137,293 B2 | 3/2012 | Zhou et al. |
| 8,167,821 B2 | 5/2012 | Sharrow |
| 8,257,279 B2 | 9/2012 | Jacobsen |
| 8,292,827 B2 | 10/2012 | Musbach et al. |
| 8,292,828 B2 | 10/2012 | Uihlein |
| 8,357,140 B2 | 1/2013 | Majercak et al. |
| 8,376,865 B2 | 2/2013 | Forster et al. |
| 8,376,961 B2 | 2/2013 | Layman et al. |
| 8,377,056 B2 | 2/2013 | Oyola et al. |
| 8,409,114 B2 | 4/2013 | Parins |
| 8,409,169 B1 | 4/2013 | Moss |
| 8,444,577 B2 | 5/2013 | Bunch et al. |
| 8,454,535 B2 | 6/2013 | Majercak et al. |
| 8,460,213 B2 | 6/2013 | Northrop |
| 8,465,469 B2 | 6/2013 | Brightbill |
| 8,468,919 B2 | 6/2013 | Christian et al. |
| 8,500,658 B2 | 8/2013 | Boyle et al. |
| 8,517,959 B2 | 8/2013 | Kurosawa et al. |
| 8,535,243 B2 | 9/2013 | Shireman |
| 8,540,648 B2 | 9/2013 | Uihlein |
| 8,540,668 B2 | 9/2013 | Griffin et al. |
| 8,551,020 B2 | 10/2013 | Chen et al. |
| 8,551,021 B2 | 10/2013 | Voeller et al. |
| 8,556,914 B2 | 10/2013 | Vrba |
| 8,585,643 B2 | 11/2013 | Vo et al. |
| 8,622,931 B2 | 1/2014 | Teague et al. |
| 8,622,933 B2 | 1/2014 | Maki et al. |
| 8,728,075 B2 | 5/2014 | Wu et al. |
| 8,758,269 B2 | 6/2014 | Miyata et al. |
| 8,784,337 B2 | 7/2014 | Voeller et al. |
| 8,795,202 B2 | 8/2014 | Northrop et al. |
| 8,795,254 B2 | 8/2014 | Layman et al. |
| 8,821,477 B2 | 9/2014 | Northrop et al. |
| 8,870,790 B2 | 10/2014 | Davis et al. |
| 8,900,163 B2 | 12/2014 | Jacobsen et al. |
| 8,915,865 B2 | 12/2014 | Jacobsen et al. |
| 8,932,235 B2 | 1/2015 | Jacobsen et al. |
| 8,936,558 B2 | 1/2015 | Jacobsen et al. |
| 8,939,916 B2 | 1/2015 | Jacobsen et al. |
| 8,956,310 B2 | 2/2015 | Miyata et al. |
| 9,011,511 B2 | 4/2015 | Gregorich et al. |
| 9,067,332 B2 | 6/2015 | Lippert et al. |
| 9,067,333 B2 | 6/2015 | Lippert et al. |
| 9,072,873 B2 | 7/2015 | Lippert et al. |
| 9,072,874 B2 | 7/2015 | Northrop et al. |
| D742,000 S | 10/2015 | Kanazawa |
| 9,162,040 B2 | 10/2015 | Vo et al. |
| 9,227,037 B2 | 1/2016 | Northrop |
| 9,364,589 B2 | 6/2016 | Cage et al. |
| 9,375,234 B2 | 6/2016 | Vrba |
| 9,433,762 B2 | 9/2016 | Griffin et al. |
| 9,439,557 B2 | 9/2016 | Boulais |
| 9,550,013 B2 | 1/2017 | Kawasaki |
| 9,616,195 B2 | 4/2017 | Lippert et al. |
| 9,623,212 B2 | 4/2017 | Tano et al. |
| 9,662,798 B2 | 5/2017 | Christian et al. |
| 9,700,702 B2 | 7/2017 | Tano et al. |
| 9,808,595 B2 | 11/2017 | Turnlund et al. |
| 9,839,764 B2 | 12/2017 | Chouinard |
| 9,848,882 B2 | 12/2017 | Lippert |
| D809,138 S | 1/2018 | Khan et al. |
| 9,950,137 B2 | 4/2018 | Lippert et al. |
| 9,999,748 B2 | 6/2018 | Cajamarca et al. |
| 10,028,666 B2 | 7/2018 | Gregorich |
| 10,052,013 B2 | 8/2018 | Boulais |
| 10,149,608 B2 | 12/2018 | Fujitani |
| D839,426 S | 1/2019 | Bajwa |
| D847,335 S | 4/2019 | Kuwada |
| 10,252,024 B2 | 4/2019 | Northrop |
| D855,180 S | 7/2019 | Haefliger |
| 10,350,383 B2 | 7/2019 | Shuman |
| 10,363,389 B2 | 7/2019 | Lippert et al. |
| D855,800 S | 8/2019 | Gabay et al. |
| 10,420,537 B2 | 9/2019 | Salahieh et al. |
| 10,456,556 B2 | 10/2019 | Cabiri |
| 10,639,456 B2 | 5/2020 | Peralta |
| 10,675,444 B2 | 6/2020 | Kauphusman et al. |
| 10,758,710 B2 | 9/2020 | Romano |
| 10,806,893 B2 | 10/2020 | Jaroch |
| 11,007,345 B2 | 5/2021 | Cottone |
| 11,052,226 B2 | 7/2021 | Salahieh et al. |
| 11,141,566 B2 | 10/2021 | Cabiri |
| D946,148 S | 3/2022 | Takemoto |
| 11,278,704 B2 | 3/2022 | Pleijers |
| 11,471,645 B2 | 10/2022 | McNiven et al. |
| 11,497,512 B2 | 11/2022 | Wallace et al. |
| 11,565,093 B2 | 1/2023 | Kirt et al. |
| D980,427 S | 3/2023 | Method et al. |
| 11,679,236 B2 | 6/2023 | Von et al. |
| 11,724,065 B2 | 8/2023 | Tilson et al. |
| 11,724,068 B2 | 8/2023 | Von et al. |
| 11,759,217 B2 | 9/2023 | Keating et al. |
| 11,766,539 B2 | 9/2023 | Yee et al. |
| D1,014,751 S | 2/2024 | Shih |
| 11,918,753 B2 | 3/2024 | Moquin et al. |
| 11,957,312 B2 | 4/2024 | Boulais |
| 2001/0009980 A1 | 7/2001 | Richardson et al. |
| 2001/0044624 A1 | 11/2001 | Seraj et al. |
| 2002/0013540 A1 | 1/2002 | Jacobsen et al. |
| 2002/0019599 A1 | 2/2002 | Rooney et al. |
| 2002/0049392 A1 | 4/2002 | Demello |
| 2002/0062524 A1 | 5/2002 | Vogland et al. |
| 2002/0068912 A1 | 6/2002 | Merdan |
| 2002/0078808 A1 | 6/2002 | Jacobsen et al. |
| 2002/0082524 A1 | 6/2002 | Anderson et al. |
| 2003/0009208 A1 | 1/2003 | Snyder et al. |
| 2003/0023190 A1 | 1/2003 | Cox |
| 2003/0060732 A1 | 3/2003 | Jacobsen et al. |
| 2003/0069521 A1 | 4/2003 | Reynolds et al. |
| 2003/0069522 A1* | 4/2003 | Jacobsen ........... A61M 25/0051 600/585 |
| 2003/0093059 A1 | 5/2003 | Griffin et al. |
| 2003/0125641 A1 | 7/2003 | Jafari et al. |
| 2004/0039371 A1 | 2/2004 | Tockman et al. |
| 2004/0054349 A1 | 3/2004 | Brightbill |
| 2004/0087933 A1 | 5/2004 | Lee et al. |
| 2004/0093060 A1 | 5/2004 | Seguin et al. |
| 2004/0102719 A1 | 5/2004 | Keith et al. |
| 2004/0102720 A1 | 5/2004 | Kellerman et al. |
| 2004/0111044 A1 | 6/2004 | Davis et al. |

(56) References Cited

U.S. PATENT DOCUMENTS

| | | |
|---|---|---|
| 2004/0122340 A1 | 6/2004 | Vrba et al. |
| 2004/0167437 A1 | 8/2004 | Sharrow et al. |
| 2004/0167440 A1 | 8/2004 | Sharrow |
| 2004/0167443 A1 | 8/2004 | Shireman et al. |
| 2004/0171996 A1 | 9/2004 | Kiemeneij |
| 2004/0181174 A2 | 9/2004 | Davis et al. |
| 2004/0186485 A1 | 9/2004 | Kear |
| 2004/0193140 A1 | 9/2004 | Griffin et al. |
| 2004/0225292 A1 | 11/2004 | Sasso et al. |
| 2004/0254450 A1 | 12/2004 | Griffin et al. |
| 2005/0054953 A1 | 3/2005 | Ryan et al. |
| 2005/0065456 A1 | 3/2005 | Eskuri |
| 2005/0124976 A1 | 6/2005 | Devens et al. |
| 2005/0137501 A1 | 6/2005 | Euteneuer et al. |
| 2005/0216049 A1 | 9/2005 | Jones et al. |
| 2005/0274384 A1 | 12/2005 | Tran et al. |
| 2006/0006649 A1 | 1/2006 | Galdonik et al. |
| 2006/0041186 A1 | 2/2006 | Vancaillie |
| 2006/0074442 A1 | 4/2006 | Noriega et al. |
| 2006/0089618 A1 | 4/2006 | McFerran et al. |
| 2006/0112802 A1 | 6/2006 | Fujinami |
| 2006/0121218 A1 | 6/2006 | Obara et al. |
| 2006/0189896 A1 | 8/2006 | Davis et al. |
| 2006/0241519 A1 | 10/2006 | Hojeibane et al. |
| 2006/0247661 A1 | 11/2006 | Richards et al. |
| 2006/0262474 A1 | 11/2006 | Chen et al. |
| 2007/0010786 A1 | 1/2007 | Casey et al. |
| 2007/0055302 A1 | 3/2007 | Henry et al. |
| 2007/0100285 A1 | 5/2007 | Griffin et al. |
| 2007/0112331 A1 | 5/2007 | Weber et al. |
| 2007/0135763 A1 | 6/2007 | Musbach et al. |
| 2007/0142893 A1 | 6/2007 | Buiser et al. |
| 2007/0167876 A1 | 7/2007 | Euteneuer et al. |
| 2007/0185415 A1 | 8/2007 | Ressemann et al. |
| 2007/0213689 A1 | 9/2007 | Grewe et al. |
| 2007/0221230 A1 | 9/2007 | Thompson et al. |
| 2007/0233039 A1 | 10/2007 | Mitelberg |
| 2007/0250036 A1 | 10/2007 | Volk et al. |
| 2007/0282270 A1 | 12/2007 | Mathews et al. |
| 2007/0287955 A1 | 12/2007 | Layman et al. |
| 2008/0021347 A1 | 1/2008 | Jacobsen et al. |
| 2008/0021401 A1 | 1/2008 | Jacobsen et al. |
| 2008/0021404 A1 | 1/2008 | Jacobsen et al. |
| 2008/0021406 A1 | 1/2008 | Jacobsen et al. |
| 2008/0064989 A1 | 3/2008 | Chen et al. |
| 2008/0077049 A1 | 3/2008 | Hirshman |
| 2008/0086854 A1 | 4/2008 | Boyd et al. |
| 2008/0097246 A1 | 4/2008 | Stafford |
| 2008/0097247 A1 | 4/2008 | Eskuri |
| 2008/0097248 A1 | 4/2008 | Munoz et al. |
| 2008/0114303 A1 | 5/2008 | Tremaglio |
| 2008/0119869 A1 | 5/2008 | Teague et al. |
| 2008/0122226 A1 | 5/2008 | Madison |
| 2008/0125674 A1 | 5/2008 | Bilecen et al. |
| 2008/0147170 A1 | 6/2008 | Vrba |
| 2008/0188298 A1 | 8/2008 | Seelig et al. |
| 2008/0188928 A1 | 8/2008 | Salahieh et al. |
| 2008/0200839 A1 | 8/2008 | Bunch et al. |
| 2008/0262474 A1 | 10/2008 | Northrop |
| 2008/0269641 A1 | 10/2008 | O'Shaughnessy et al. |
| 2008/0319525 A1 | 12/2008 | Tieu et al. |
| 2009/0036832 A1 | 2/2009 | Skujins et al. |
| 2009/0036833 A1 | 2/2009 | Parins |
| 2009/0043283 A1 | 2/2009 | Turnlund et al. |
| 2009/0043372 A1 | 2/2009 | Northrop et al. |
| 2009/0118675 A1 | 5/2009 | Czyscon et al. |
| 2009/0118704 A1 | 5/2009 | Sharrow et al. |
| 2009/0177119 A1 | 7/2009 | Heidner et al. |
| 2009/0177185 A1 | 7/2009 | Northrop |
| 2009/0254000 A1 | 10/2009 | Layman et al. |
| 2009/0292225 A1 | 11/2009 | Chen et al. |
| 2009/0318892 A1 | 12/2009 | Aboytes et al. |
| 2010/0063479 A1 | 3/2010 | Merdan et al. |
| 2010/0069882 A1 | 3/2010 | Jennings et al. |
| 2010/0114017 A1 | 5/2010 | Lenker et al. |
| 2010/0114302 A1 | 5/2010 | Tzafriri et al. |
| 2010/0139465 A1 | 6/2010 | Christian et al. |
| 2010/0145308 A1 | 6/2010 | Layman et al. |
| 2010/0228150 A1 | 9/2010 | Zimmerman et al. |
| 2010/0256527 A1 | 10/2010 | Lippert et al. |
| 2010/0256528 A1 | 10/2010 | Lippert et al. |
| 2010/0256601 A1 | 10/2010 | Lippert et al. |
| 2010/0256602 A1 | 10/2010 | Lippert et al. |
| 2010/0256603 A1 | 10/2010 | Lippert et al. |
| 2010/0256604 A1 | 10/2010 | Lippert et al. |
| 2010/0256605 A1 | 10/2010 | Lippert et al. |
| 2010/0256606 A1 | 10/2010 | Lippert et al. |
| 2010/0318066 A1 | 12/2010 | Miyata et al. |
| 2011/0011226 A1 | 1/2011 | Tsurusawa et al. |
| 2011/0022003 A1 | 1/2011 | Tekulve |
| 2011/0160680 A1 | 6/2011 | Cage et al. |
| 2011/0245807 A1 | 10/2011 | Sakata et al. |
| 2011/0245808 A1 | 10/2011 | Voeller et al. |
| 2011/0251519 A1 | 10/2011 | Romoscanu |
| 2011/0313417 A1* | 12/2011 | De La Rama ..... A61B 18/1492 606/41 |
| 2012/0046575 A1 | 2/2012 | Brown |
| 2012/0065623 A1 | 3/2012 | Nelson et al. |
| 2012/0158034 A1 | 6/2012 | Wilson et al. |
| 2012/0209073 A1 | 8/2012 | McWeeney et al. |
| 2012/0239074 A1 | 9/2012 | Aboytes et al. |
| 2012/0271397 A1 | 10/2012 | Muzslay et al. |
| 2012/0289938 A1 | 11/2012 | Northrop et al. |
| 2013/0018280 A1 | 1/2013 | Tano et al. |
| 2013/0018359 A1 | 1/2013 | Coyle |
| 2013/0096553 A1 | 4/2013 | Hill et al. |
| 2013/0110000 A1 | 5/2013 | Tully et al. |
| 2013/0131642 A1 | 5/2013 | Miyata et al. |
| 2013/0144267 A1 | 6/2013 | Chan et al. |
| 2013/0184703 A1 | 7/2013 | Shireman et al. |
| 2013/0226033 A1 | 8/2013 | Eskuri |
| 2013/0255456 A1 | 10/2013 | Christian et al. |
| 2014/0012281 A1 | 1/2014 | Wang et al. |
| 2014/0031719 A1 | 1/2014 | Kanazawa |
| 2014/0058324 A1 | 2/2014 | Salahieh et al. |
| 2014/0094787 A1 | 4/2014 | Reynolds |
| 2014/0187983 A1 | 7/2014 | Anderson |
| 2014/0257363 A1 | 9/2014 | Lippert |
| 2014/0276109 A1 | 9/2014 | Gregorich |
| 2014/0276787 A1 | 9/2014 | Wang et al. |
| 2014/0279109 A1 | 9/2014 | Vasquez et al. |
| 2014/0309657 A1 | 10/2014 | Ben-Ami |
| 2014/0336620 A1 | 11/2014 | Layman et al. |
| 2015/0011834 A1 | 1/2015 | Ayala et al. |
| 2015/0011964 A1 | 1/2015 | Abner et al. |
| 2015/0057639 A1 | 2/2015 | Storbeck et al. |
| 2015/0190614 A1 | 7/2015 | Uihlein |
| 2015/0190615 A1 | 7/2015 | Shaltis |
| 2015/0216533 A1 | 8/2015 | Gray et al. |
| 2015/0238734 A1 | 8/2015 | Kanazawa |
| 2015/0290432 A1 | 10/2015 | Mathews et al. |
| 2015/0297863 A1 | 10/2015 | Hannon et al. |
| 2015/0305710 A1 | 10/2015 | Stigall et al. |
| 2015/0306355 A1 | 10/2015 | Idstrom |
| 2016/0001048 A1 | 1/2016 | Koike |
| 2016/0008585 A1 | 1/2016 | Tano |
| 2016/0045101 A1 | 2/2016 | Nakatate et al. |
| 2016/0058382 A1 | 3/2016 | Burkett et al. |
| 2016/0089128 A1 | 3/2016 | Weber et al. |
| 2016/0113793 A1 | 4/2016 | Nishigishi |
| 2016/0135827 A1 | 5/2016 | Elsesser et al. |
| 2016/0199620 A1 | 7/2016 | Pokorney et al. |
| 2016/0235337 A1 | 8/2016 | Govari et al. |
| 2016/0287054 A1 | 10/2016 | Fujitani |
| 2016/0310702 A1 | 10/2016 | Cabiri |
| 2016/0361520 A1 | 12/2016 | Braun |
| 2016/0367788 A1 | 12/2016 | Jimenez et al. |
| 2016/0375226 A1 | 12/2016 | Nabeshima et al. |
| 2017/0047740 A1 | 2/2017 | Narla |
| 2017/0049594 A1 | 2/2017 | Banas et al. |
| 2017/0136213 A1 | 5/2017 | Kauphusman et al. |
| 2017/0189643 A1 | 7/2017 | Christian et al. |
| 2017/0203076 A1 | 7/2017 | Groneberg et al. |
| 2017/0215954 A1 | 8/2017 | Datta et al. |

(56) References Cited

U.S. PATENT DOCUMENTS

| | | |
|---|---|---|
| 2017/0234411 A1 | 8/2017 | Dewaele et al. |
| 2017/0281909 A1* | 10/2017 | Northrop .......... A61M 25/0013 |
| 2018/0015260 A1 | 1/2018 | Sano et al. |
| 2018/0015261 A1 | 1/2018 | Lippert et al. |
| 2018/0015262 A1 | 1/2018 | Lippert et al. |
| 2018/0015263 A1 | 1/2018 | Lippert et al. |
| 2018/0028177 A1 | 2/2018 | Van et al. |
| 2018/0071496 A1 | 3/2018 | Snyder et al. |
| 2018/0177517 A1 | 6/2018 | Lippert et al. |
| 2018/0185619 A1 | 7/2018 | Batman et al. |
| 2018/0193603 A1 | 7/2018 | Falb et al. |
| 2018/0193607 A1 | 7/2018 | Lippert et al. |
| 2018/0207407 A1 | 7/2018 | Tanigaki |
| 2019/0008639 A1* | 1/2019 | Landon ................... A61F 2/243 |
| 2019/0105463 A1 | 4/2019 | Christian et al. |
| 2019/0175869 A1 | 6/2019 | Kirt et al. |
| 2019/0255290 A1* | 8/2019 | Snyder ................ A61M 25/005 |
| 2019/0290883 A1 | 9/2019 | Lippert et al. |
| 2019/0358434 A1 | 11/2019 | Fuller et al. |
| 2020/0016378 A1 | 1/2020 | Williams et al. |
| 2020/0054860 A1 | 2/2020 | Mcelhaney et al. |
| 2020/0094027 A1 | 3/2020 | Davis |
| 2020/0121308 A1* | 4/2020 | Davis ................. A61M 25/0051 |
| 2020/0222666 A1 | 7/2020 | Chan et al. |
| 2020/0222672 A1 | 7/2020 | Davis et al. |
| 2020/0330734 A1 | 10/2020 | Sugita et al. |
| 2020/0345975 A1 | 11/2020 | Snyder |
| 2021/0022748 A1 | 1/2021 | Lorenzo |
| 2021/0162184 A1 | 6/2021 | Lippert et al. |
| 2021/0178128 A1 | 6/2021 | Lippert et al. |
| 2021/0213241 A1 | 7/2021 | Christian et al. |
| 2021/0228845 A1 | 7/2021 | Lippert et al. |
| 2021/0283372 A1 | 9/2021 | Murphy |
| 2021/0283380 A1 | 9/2021 | Lippert et al. |
| 2021/0307766 A1* | 10/2021 | Keating ................. A61B 17/22 |
| 2021/0346656 A1 | 11/2021 | Lippert et al. |
| 2022/0039644 A1 | 2/2022 | Dayton et al. |
| 2022/0047845 A1 | 2/2022 | Niederhauser et al. |
| 2022/0105318 A1 | 4/2022 | Davis et al. |
| 2022/0118225 A1 | 4/2022 | Snyder et al. |
| 2022/0176075 A1 | 6/2022 | McDermott et al. |
| 2022/0211981 A1 | 7/2022 | Darbellay et al. |
| 2022/0218358 A1 | 7/2022 | Dagan et al. |
| 2022/0273474 A1 | 9/2022 | Koop et al. |
| 2022/0280147 A1 | 9/2022 | Davis |
| 2022/0296850 A1 | 9/2022 | Lippert |
| 2022/0323166 A1 | 10/2022 | Tilson et al. |
| 2022/0378459 A1 | 12/2022 | Lippert |
| 2023/0010697 A1 | 1/2023 | Sharma et al. |
| 2023/0069698 A1 | 3/2023 | Hallauer et al. |
| 2023/0071512 A1 | 3/2023 | Maggio et al. |
| 2023/0082226 A1 | 3/2023 | Lippert et al. |
| 2023/0285720 A1 | 9/2023 | Isogai |
| 2023/0405276 A1 | 12/2023 | Cabiri |
| 2024/0123196 A1 | 4/2024 | Lippert et al. |
| 2024/0198059 A1 | 6/2024 | Lippert et al. |
| 2024/0299710 A1 | 9/2024 | Davis et al. |

FOREIGN PATENT DOCUMENTS

| | | |
|---|---|---|
| AU | 07745/59 B2 | 7/2004 |
| AU | 2008229892 A1 | 10/2008 |
| BR | 9709363 A | 1/2000 |
| BR | 9712829 A | 1/2000 |
| CA | 2255781 A1 | 11/1997 |
| CA | 2266685 A1 | 3/1998 |
| CA | 2395149 A1 | 6/2001 |
| CN | 1225282 A | 8/1999 |
| CN | 1230914 A | 10/1999 |
| CN | 1324285 A | 11/2001 |
| CN | 1422673 A | 6/2003 |
| CN | 1518428 A | 8/2004 |
| CN | 1781684 A | 6/2006 |
| CN | 1897892 A | 1/2007 |
| CN | 101001660 A | 7/2007 |
| CN | 101209365 A | 7/2008 |
| CN | 101304778 A | 11/2008 |
| CN | 201239164 Y | 5/2009 |
| CN | 101815553 A | 8/2010 |
| CN | 102049085 A | 5/2011 |
| CN | 102107041 A | 6/2011 |
| CN | 102548603 A | 7/2012 |
| CN | 102639303 A | 8/2012 |
| CN | 102824681 A | 12/2012 |
| CN | 102847225 A | 1/2013 |
| CN | 103301553 A | 9/2013 |
| CN | 103764012 A | 4/2014 |
| CN | 103860265 A | 6/2014 |
| CN | 104271035 A | 1/2015 |
| CN | 104427950 A | 3/2015 |
| CN | 104602616 A | 5/2015 |
| CN | 104602718 A | 5/2015 |
| CN | 104759022 A | 7/2015 |
| CN | 105209102 A | 12/2015 |
| CN | 105361918 A | 3/2016 |
| CN | 105545375 A | 5/2016 |
| CN | 105582611 A | 5/2016 |
| CN | 105682725 A | 6/2016 |
| CN | 105682729 A | 6/2016 |
| CN | 105828690 A | 8/2016 |
| CN | 105979880 A | 9/2016 |
| CN | 107206216 A | 9/2017 |
| CN | 109125889 A | 1/2019 |
| CN | 109715245 A | 5/2019 |
| CN | 109789296 A | 5/2019 |
| DE | 60036882 T2 | 7/2008 |
| DE | 69738235 T2 | 7/2008 |
| EP | 0521595 A2 | 1/1993 |
| EP | 0921754 A1 | 6/1999 |
| EP | 0998323 A1 | 5/2000 |
| EP | 0934141 B1 | 11/2005 |
| EP | 1239901 B1 | 10/2007 |
| EP | 1844911 A1 | 10/2007 |
| EP | 1940498 A1 | 7/2008 |
| EP | 2964305 A2 | 1/2016 |
| EP | 2414022 B1 | 8/2017 |
| EP | 3866902 A1 | 8/2021 |
| ES | 2293660 T3 | 3/2008 |
| GB | 2478988 A | 9/2011 |
| JP | 59-102509 A | 6/1984 |
| JP | 06-154335 A | 6/1994 |
| JP | 07-008560 A | 1/1995 |
| JP | 08-215313 A | 8/1996 |
| JP | 08-243169 A | 9/1996 |
| JP | 08-308934 A | 11/1996 |
| JP | 09-288239 A | 11/1997 |
| JP | 11-294497 A | 10/1999 |
| JP | 2000-116787 A | 4/2000 |
| JP | 2000-126301 A | 5/2000 |
| JP | 2000-511094 A | 8/2000 |
| JP | 2000-343313 A | 12/2000 |
| JP | 2001-500808 A | 1/2001 |
| JP | 2002-543896 A | 12/2002 |
| JP | 2003-011117 A | 1/2003 |
| JP | 2004-025340 A | 1/2004 |
| JP | 2004-136121 A | 5/2004 |
| JP | 2004-329552 A | 11/2004 |
| JP | 2004-535233 A | 11/2004 |
| JP | 2005-514115 A | 5/2005 |
| JP | 2005-533594 A | 11/2005 |
| JP | 2005-534407 A | 11/2005 |
| JP | 2007-514458 A | 6/2007 |
| JP | 2007-313638 A | 12/2007 |
| JP | 2008-178656 A | 8/2008 |
| JP | 2008-536639 A | 9/2008 |
| JP | 2010-029736 A | 2/2010 |
| JP | 2010-503484 A | 2/2010 |
| JP | 2010-535583 A | 11/2010 |
| JP | 2010-535588 A | 11/2010 |
| JP | 2011-206175 A | 10/2011 |
| JP | 4805208 B2 | 11/2011 |
| JP | 4845313 B2 | 12/2011 |
| JP | 2012-502743 A | 2/2012 |
| JP | 2012-522607 A | 9/2012 |

(56) References Cited

FOREIGN PATENT DOCUMENTS

| | | | |
|---|---|---|---|
| JP | 2013-106854 | A | 6/2013 |
| JP | 2013-523282 | A | 6/2013 |
| JP | 2013-176560 | A | 9/2013 |
| JP | 2014-023727 | A | 2/2014 |
| JP | 2015-073861 | A | 4/2015 |
| JP | 2015-181723 | A | 10/2015 |
| JP | 2015-186427 | A | 10/2015 |
| JP | 2016-013269 | A | 1/2016 |
| JP | 2017-169253 | A | 9/2017 |
| KR | 2000-0015896 | A | 3/2000 |
| KR | 10-2000-0036139 | A | 6/2000 |
| NL | 2017570 | B1 | 4/2018 |
| RU | 91674 | U1 | 2/2010 |
| TW | 412468 | B | 11/2000 |
| WO | 94/06503 | A1 | 3/1994 |
| WO | 94/19039 | A1 | 9/1994 |
| WO | 95/24237 | A2 | 9/1995 |
| WO | 97/43949 | A1 | 11/1997 |
| WO | 98/55173 | A1 | 12/1998 |
| WO | 98/58697 | A1 | 12/1998 |
| WO | 99/04847 | A1 | 2/1999 |
| WO | 99/53824 | A2 | 10/1999 |
| WO | 2004/011076 | A2 | 2/2004 |
| WO | 2006/025931 | A1 | 3/2006 |
| WO | 2006/058234 | A2 | 6/2006 |
| WO | 2006/113863 | A2 | 10/2006 |
| WO | 2007/050718 | A1 | 5/2007 |
| WO | 2008/034010 | A2 | 3/2008 |
| WO | 2009/020691 | A2 | 2/2009 |
| WO | 2009/020836 | A1 | 2/2009 |
| WO | 2009/020961 | A1 | 2/2009 |
| WO | 2009/020962 | A1 | 2/2009 |
| WO | 2009/058705 | A2 | 5/2009 |
| WO | 2009/143160 | A1 | 11/2009 |
| WO | 2010/077692 | A2 | 7/2010 |
| WO | 2010/115163 | A1 | 10/2010 |
| WO | 2011/123689 | A1 | 10/2011 |
| WO | 2014/005095 | A1 | 1/2014 |
| WO | 2014/066104 | A1 | 5/2014 |
| WO | 2014/138580 | A2 | 9/2014 |
| WO | 2016/047499 | A1 | 3/2016 |
| WO | 2016/117238 | A1 | 7/2016 |
| WO | 2016/136609 | A1 | 9/2016 |
| WO | 2016/152194 | A1 | 9/2016 |
| WO | 2016/158671 | A1 | 10/2016 |
| WO | 2017/151292 | A1 | 9/2017 |
| WO | 2018/017349 | A1 | 1/2018 |
| WO | 2018/017351 | A1 | 1/2018 |
| WO | 2018/052815 | A1 | 3/2018 |
| WO | 2018/218216 | | 11/2018 |
| WO | 2020/217171 | A1 | 10/2020 |
| WO | 2021/150920 | A1 | 7/2021 |
| WO | 2022/159139 | A1 | 7/2022 |

OTHER PUBLICATIONS

Final Office Action received for U.S. Appl. No. 12/753,831, mailed on May 31, 2012.
Final Office Action received for U.S. Appl. No. 12/753,836 mailed on Feb. 17, 2016.
Final Office Action received for U.S. Appl. No. 16/212,425, mailed on Aug. 3, 2020, 14 pages.
Final Office Action received for U.S. Appl. No. 12/753,831, mailed on Aug. 29, 2014.
Final Office Action received for U.S. Appl. No. 12/753,836, mailed on Jan. 9, 2015.
Final Office Action received for U.S. Appl. No. 12/753,836, mailed on Jul. 14, 2017.
Final Office Action received for U.S. Appl. No. 12/753,836, mailed on May 1, 2012.
Final Office Action received for U.S. Appl. No. 12/753,839, mailed on May 31, 2012.
Final Office Action received for U.S. Appl. No. 12/753,842, mailed on Jan. 9, 2013.
Final Office Action received for U.S. Appl. No. 12/753,842, mailed on Sep. 4, 2014.
Final Office Action received for U.S. Appl. No. 12/753,849, mailed on Jun. 6, 2012.
Final Office Action received for U.S. Appl. No. 12/753,849, mailed on Oct. 9, 2013.
Final Office Action received for U.S. Appl. No. 12/753,855, mailed on Apr. 18, 2012.
Final Office Action received for U.S. Appl. No. 12/753,855, mailed on Jan. 13, 2015.
Final Office Action received for U.S. Appl. No. 12/753,858, mailed on Jan. 17, 2014.
Final Office Action received for U.S. Appl. No. 12/753,858, mailed on Jul. 18, 2012.
Final Office Action received for U.S. Appl. No. 12/753,858, mailed on May 28, 2015.
Final Office Action received for U.S. Appl. No. 12/753,858, mailed on Nov. 14, 2018.
Final Office Action received for U.S. Appl. No. 12/753,858, mailed on Oct. 19, 2011.
Final Office Action received for U.S. Appl. No. 12/753,858, mailed on Oct. 20, 2017.
Final Office Action received for U.S. Appl. No. 15/606,607, mailed on Nov. 19, 2019.
Final Office Action received for U.S. Appl. No. 15/611,344, mailed on Nov. 12, 2019.
Final Office Action received for U.S. Appl. No. 15/848,878, mailed on Aug. 27, 2020, 13 pages.
Final Office Action received for U.S. Appl. No. 15/848,878, mailed on Sep. 22, 2021, 12 pages.
Final Office Action received for U.S. Appl. No. 16/281,046, mailed on May 11, 2021, 18 pages.
Final Office Action received for U.S. Appl. No. 16/616,220, mailed on Oct. 12, 2022, 17 pages.
Final Office Action received for U.S. Appl. No. 16/742,211, mailed on Mar. 14, 2023, 22 pages.
Final Office Action received for U.S. Appl. No. 16/855,366, mailed on Dec. 8, 2022, 18 pages.
Final Office Action received for U.S. Appl. No. 17/216,127, mailed on Jun. 13, 2022, 8 pages.
Final Office Action received for U.S. Appl. No. 14/199,675, mailed on May 18, 2017.
Final Office Action received for U.S. Appl. No. 15/611,328, mailed on Sep. 24, 2019.
Final Office Action received for U.S. Appl. No. 15/698,553, mailed on Nov. 27, 2019.
Final Rejection received for U.S. Appl. No. 15/606,607, mailed on Dec. 15, 2020, 24 pages.
International Search Report and Written Opinion for application No. PCT/US17/41305 dated Oct. 2, 2017.
International Search Report and Written Opinion for Application PCT/US2017/050602 mailed on Nov. 7, 2017.
International Search Report and Written Opinion for PCT/US2009/067217 dated Dec. 16, 2010.
International Search Report and Written Opinion for PCT/US2010/029867 dated Jun. 1, 2010.
International Search Report and Written Opinion for PCT/US2014/021742 dated Aug. 27, 2014.
International Search Report and Written Opinion for PCT/US2017/041299 mailed on Oct. 2, 2017.
International Search Report and Written Opinion for PCT/US2017/041301 mailed on Oct. 2, 2017.
International Search Report and Written Opinion for PCT/US2017/068056 mailed on Feb. 26, 2018.
International Search Report and Written Opinion for PCT/US2018/034756 mailed on Aug. 14, 2018.
International Search Report and Written Opinion for PCT/US2019/019046, mailed on May 17, 2019.
International Search Report and Written Opinion for PCT/US2019/021031 mailed on Jun. 18, 2019.
International Search Report and Written Opinion issued in PCT/US2018/034723 mailed Sep. 5, 2018.

(56) References Cited

OTHER PUBLICATIONS

InternationalSearch Report and Written Opinion for application PCT/US2017/050802 mailed on Nov. 7, 2017.
Non-Final Office Action received for U.S. Appl. No. 15/606,607, mailed on Jun. 10, 2020, 26 pages.
Non-Final Office Action received for U.S. Appl. No. 15/611,328, mailed on Jun. 29, 2020, 13 pages.
Non-Final Office Action received for U.S. Appl. No. 15/848,878, mailed on Jun. 3, 2021, 13 pages.
Non-Final Office Action received for U.S. Appl. No. 15/917,255, mailed on Aug. 17, 2020, 12 pages.
International Search Report and Written Opinion received for PCT Patent Application No. PCT/US22/42514, mailed on Dec. 28, 2022, 11 pages.
International Search Report and Written Opinion received for PCT Patent Application No. PCT/US22/42517, mailed on Feb. 7, 2023, 11 pages.
International Search Report and Written Opinion received for PCT Patent Application No. PCT/US2009/067217, mailed on Dec. 16, 2010, 10 pages.
International Search Report and Written Opinion received for PCT Patent Application No. PCT/US2010/029867, mailed on Jun. 1, 2010, 15 pages.
International Search Report and Written Opinion received for PCT Patent Application No. PCT/US2018/034723, mailed on Sep. 5, 2018, 10 pages.
International Search Report and Written Opinion received for PCT Patent Application No. PCT/US2018/034756, mailed on Aug. 14, 2018, 12 pages.
International Search Report and Written Opinion received for PCT Patent Application No. PCT/US2019/019046, mailed on May 17, 2019, 14 pages.
International Search Report and Written Opinion received for PCT Patent Application No. PCT/US2020/030589, mailed on Jul. 17, 2020, 7 pages.
International Search Report and Written Opinion received for PCT Patent Application No. PCT/US2021/053652, mailed on Dec. 28, 2021, 9 pages.
International Search Report and Written Opinion received for PCT Patent Application No. PCT/US21/042753, mailed on Nov. 5, 2021, 14 pages.
International Search Report and Written Opinion received for PCT Patent Application No. PCT/US21/14656, mailed on Apr. 28, 2021, 8 pages.
International Search Report and Written Opinion, PCT App. No. PCT/US2020/013754, mailed on Jun. 9, 2020, 11 pages.
Non-Final Office Action received for U.S. Appl. No. 16/281,046, mailed on Oct. 29, 2020, 18 pages.
Non-Final Office Action received for U.S. Appl. No. 16/616, 139, mailed on Oct. 26, 2021, 11 pages.
Non-Final Office Action received for U.S. Appl. No. 16/616,220, mailed on Jun. 3, 2022, 20 pages.
Non-Final Office Action received for U.S. Appl. No. 16/742,211, mailed on Aug. 15, 2022, 20 pages.
Non-Final Office Action received for U.S. Appl. No. 16/855,366, mailed on Jul. 11, 2022, 13 pages.
Non-Final Office Action received for U.S. Appl. No. 16/855,366, mailed on Jun. 23, 2021, 15 pages.
Non-Final Office Action received for U.S. Appl. No. 17/177,782, mailed on Jan. 23, 2023, 14 pages.
Non-Final Office Action received for U.S. Appl. No. 17/177,782, mailed on Nov. 4, 2022, 7 pages.
Notice of Allowance received for U.S. Appl. No. 16/212,425, mailed on Dec. 23, 2020, 12 pages.
Notice of Allowance received for U.S. Appl. No. 16/212,425, mailed on Jan. 25, 2021, 2 pages.
Office Action received for U.S. Appl. No. 12/633,727, mailed on Oct. 16, 2012.
Office Action received for U.S. Appl. No. 12/753,831, mailed on Feb. 1, 2012.
Office Action received for U.S. Appl. No. 12/753,831, mailed on Mar. 21, 2014.
Office Action received for U.S. Appl. No. 12/753,836, mailed on Dec. 9, 2011.
Office Action received for U.S. Appl. No. 12/753,836, mailed on Dec. 23, 2016.
Office Action received for U.S. Appl. No. 12/753,836, mailed on Jul. 31, 2014.
Office Action received for U.S. Appl. No. 12/753,836, mailed on Jun. 26, 2015.
Office Action received for U.S. Appl. No. 12/753,839, mailed on Feb. 7, 2012.
Office Action received for U.S. Appl. No. 12/753,839, mailed on May 5, 2014.
Office Action received for U.S. Appl. No. 12/753,842, mailed on Aug. 1, 2012.
Office Action received for U.S. Appl. No. 12/753,842, mailed on Jan. 29, 2014.
Office Action received for U.S. Appl. No. 12/753,849, mailed on Jan. 3, 2013.
Office Action received for U.S. Appl. No. 12/753,849, mailed on May 10, 2011.
Office Action received for U.S. Appl. No. 12/753,849, mailed on May 27, 2014.
Office Action received for U.S. Appl. No. 12/753,849, mailed on Oct. 18, 2011.
Office Action received for U.S. Appl. No. 12/753,855, mailed on Feb. 28, 2014.
Office Action received for U.S. Appl. No. 12/753,855, mailed on May 21, 2015.
Office Action received for U.S. Appl. No. 12/753,855, mailed on Sep. 15, 2011.
Office Action received for U.S. Appl. No. 12/753,858, mailed on Dec. 30, 2015.
Office Action received for U.S. Appl. No. 12/753,858, mailed on Feb. 3, 2012.
Office Action received for U.S. Appl. No. 12/753,858, mailed on Mar. 13, 2018.
Office Action received for U.S. Appl. No. 12/753,858, mailed on Mar. 27, 2017.
Office Action received for U.S. Appl. No. 12/753,858, mailed on Mar. 29, 2013.
Office Action received for U.S. Appl. No. 12/753,858, mailed on May 10, 2011.
Office Action received for U.S. Appl. No. 12/753,858, mailed on Oct. 24, 2016.
Office Action received for U.S. Appl. No. 12/753,858, mailed on Sep. 4, 2014.
Office Action received for U.S. Appl. No. 13/901,375, mailed on Dec. 10, 2015.
Office Action received for U.S. Appl. No. 15/465,399, mailed on Apr. 23, 2018.
Office Action received for U.S. Appl. No. 15/606,607, mailed on May 14, 2019.
Office Action received for U.S. Appl. No. 15/611,344, mailed on Mar. 26, 2019.
Office Action received for U.S. Appl. No. 15/611,344, mailed on May 21, 2020.
Office Action received for U.S. Appl. No. 15/848,878, mailed on Feb. 5, 2020.
Office Action received for U.S. Appl. No. 15/848,878, mailed on Oct. 29, 2019.
Office Action received for U.S. Appl. No. 16/212,425, mailed on Mar. 16, 2020.
Office Action received for U.S. Appl. No. 12/753,855 mailed on May 5, 2016.
Office Action received for U.S. Appl. No. 13/901,375, mailed on Aug. 1, 2016.
Office Action received for U.S. Appl. No. 14/199,675, mailed on Nov. 3, 2016.
Office Action received for U.S. Appl. No. 15/611,328, mailed on Mar. 27, 2019.

(56) References Cited

OTHER PUBLICATIONS

Penumbra Augments Vascular Franchise with Latest Indigo System Launch and Expands Medical/Scientific Leadership, Jul. 14, 2020, https://investors.penumbrainc.com/investors-relations/press-releases/press-release-details/2020/Penumbra-Augments-Vascular-Franchise-with-Latest-Indigo-System-Launch-and-Expands-MedicalScientific-Leadership/default.spx.
Office Action received for European Patent Application No. 19710207.2, mailed on Dec. 4, 2023, 4 pages.
Supplementary European Search Report received for EP Patent Application No. 21744674.9, mailed on Feb. 7, 2024, 9 pages.
European Search Report received for EP Patent Application No. 21878402, mailed on Aug. 14, 2024, 13 pages.
Final Office Action received for U.S. Appl. No. 17/382,271, mailed on Sep. 16, 2024, 9 pages.
Non-Final Office Action received for U.S. Appl. No. 17/752,600, mailed on Sep. 10, 2024, 11 pages.
Requirement for Restriction/Election received for U.S. Appl. No. 17/493,281, mailed on Oct. 9, 2024, 13 pages.
Final Office Action received for U.S. Appl. No. 16/855,366, mailed on Jun. 20, 2024, 17 pages.
Final Office Action received for U.S. Appl. No. 17/154,777, mailed on Apr. 17, 2024, 17 pages.
Final Office Action received for U.S. Appl. No. 17/836,863, mailed on Jun. 25, 2024, 6 pages.
Non-Final Office Action received for U.S. Appl. No. 17/382,271, mailed on May 14, 2024, 22 pages.
Non-Final Office Action received for U.S. Appl. No. 16/616,220, mailed on Nov. 5, 2024, 24 pages.
Non-Final Office Action received for U.S. Appl. No. 18/661,472, mailed on Dec. 6, 2024, 20 pages.
Requirement for Restriction/Election received for U.S. Appl. No. 18/589,282, mailed on Dec. 30, 2024, 5 pages.

\* cited by examiner

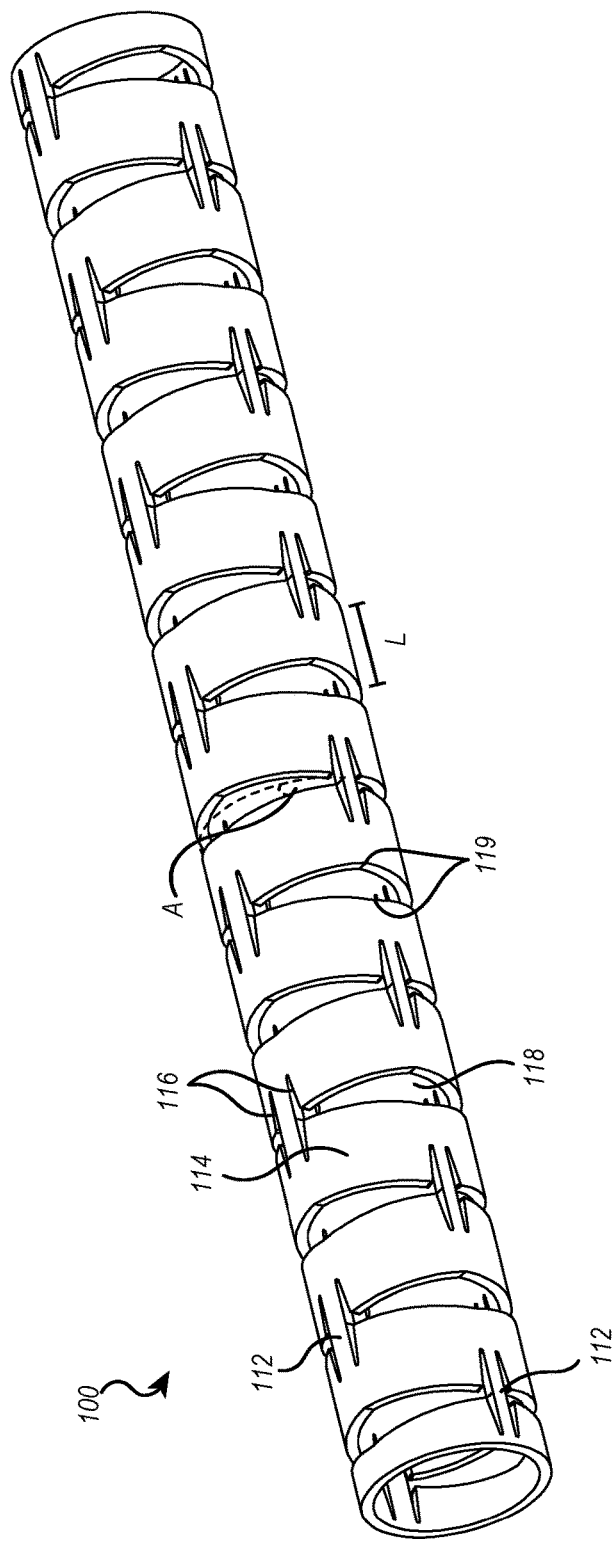
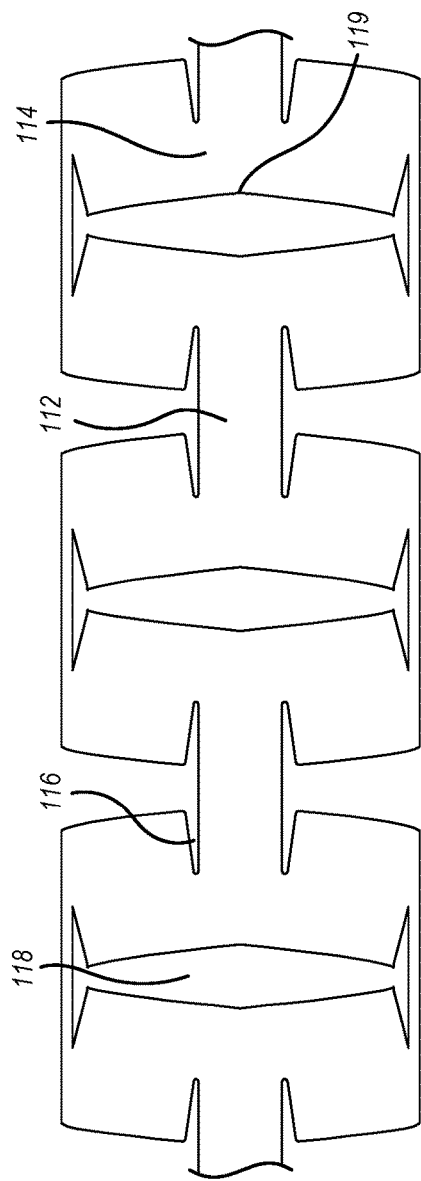
FIG. 5A
FIG. 5B

MICROFABRICATED CATHETER DEVICES WITH HIGH AXIAL STRENGTH

CROSS-REFERENCE TO RELATED APPLICATIONS

This application claims priority to and the benefit of U.S. Provisional Patent Application Ser. No. 63/087,410, filed Oct. 5, 2020, and titled "Microfabricated Catheter Devices with High Axial Strength." The entirety of the foregoing application is incorporated herein by this reference.

BACKGROUND

Guidewires and catheters are frequently utilized in the medical field to perform delicate procedures deep within the vasculature of the body. Typically, a catheter is inserted into a patient's femoral, radial, carotid, or jugular vessel and navigated through the patient's vasculature to the heart, brain, or other targeted anatomy. Often, a guidewire is first routed to the targeted anatomy, and one or more catheters are subsequently passed over the guidewire and routed to the desired location. Once in place, the catheter can be used to aspirate clots or other occlusions, or to deliver drugs, stents, embolic devices, radiopaque dyes, or other devices or substances for treating the patient.

In many applications, such catheters must be routed through tortuous bends and curves of a vasculature pathways to arrive at the targeted anatomy. Ideally, these catheters include design features that enable effective navigation of such tortuous pathways. For example, a catheter should be flexible enough to navigate the bends of the vasculature, but should also be able to provide sufficient pushability (i.e., the ability to transmit axial forces from proximal portions to distal portions) and torquability (i.e., the ability to transmit torque from proximal portions to distal portions).

If a catheter lacks sufficient axial stiffness, for example, it can be difficult for the operator to push the catheter forward through the vasculature. That is, axial forces applied at the proximal end by the operator may cause the catheter to axially compress and "accordion" rather than be effectively transmitted to the distal end of the catheter. Designing the catheter to have higher axial stiffness can alleviate this problem. However, increasing the axial stiffness of the catheter can cause other problems that interfere with effectiveness of the catheter. For example, increasing the axial stiffness of the catheter usually also increases the bending stiffness of the catheter, which can be detrimental if insufficient bending flexibility remains in the device.

Accordingly, there is an ongoing need for catheter devices with features that are designed to allow for effective axial stiffness without overly disrupting needed characteristics, such as the flexibility and torquability of the device.

SUMMARY

The present disclosure describes microfabricated intravascular devices that are configured for high axial strength while also maintaining effective bending flexibility.

In one embodiment, a tube member includes a series of circumferentially extending rings connected to one another by a series of axially extending beams. A plurality of transverse cuts separate and define the rings. The transverse cuts are disposed between adjacent rings and extend in a direction transverse to the longitudinal axis of the tube member, but not so far as to completely cut through the tube member, thereby leaving beams positioned between the rings.

In some embodiments, at least a portion of the transverse cuts are wedge-shaped. For example, one or more transverse cuts may be narrower near the corresponding beams and then widen while circumferentially extending away from the corresponding beams.

In some embodiments, a series of axial cuts are aligned with the beams and extend from the beams partially into the adjoining rings so that the beam length is nested partially within the axial length of the adjoining rings. This increases the functional length of the beams to provide bending flexibility while still sufficient ring structure to provide effective axial stiffness.

In some embodiments, at least a portion of the axial cuts are wedge-shaped. For example, one or more axial cuts may be wider at an edge of the adjoining ring and then narrow while extending along the axial direction into the adjoining ring.

This summary is provided to introduce a selection of concepts in a simplified form that are further described below in the detailed description. This summary is not intended to identify key features or essential features of the claimed subject matter, nor is it intended to be used as an indication of the scope of the claimed subject matter.

BRIEF DESCRIPTION OF THE DRAWINGS

Various objects, features, characteristics, and advantages of the invention will become apparent and more readily appreciated from the following description of the embodiments, taken in conjunction with the accompanying drawings and the appended claims, all of which form a part of this specification. In the Drawings, like reference numerals may be utilized to designate corresponding or similar parts in the various Figures, and the various elements depicted are not necessarily drawn to scale, wherein:

FIGS. 5A and 5B illustrate an exemplary microfabricated catheter section with a cut pattern that provides effective axial stiffness without overly increasing bending stiffness and thereby provides a high axial stiffness to bending stiffness ratio.

DETAILED DESCRIPTION

Introduction

Figure 1:
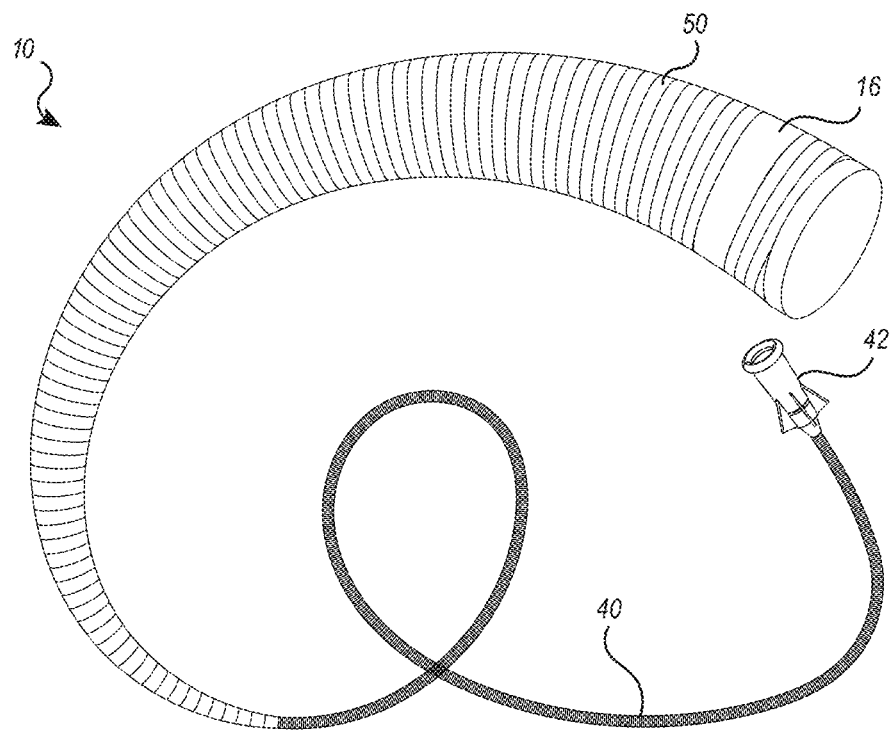
FIG. 1 illustrates an exemplary catheter device that may be modified with the cut pattern described herein to provide a catheter having high axial strength.

FIG. 1 illustrates an example of a conventional catheter device 10 that can be improved by incorporation of the unique, high push strength cut patterns described below. The catheter device 10 includes a proximal section 40 and a distal section 50. A radiopaque marker 16 may be located near the distal end. A hub and/or port 42 may be located at the proximal end. Due to the particular benefits of the high push strength designs in catheter applications, most of the examples described herein will refer to catheter devices. However, it will be understood that, in some embodiments, the same features may be applied to other microfabricated components of other intravascular devices such as guidewires.

At least part of the distal section 50 is microfabricated with one or more cut patterns intended to increase the effectiveness of the device. Conventionally, such cut patterns have focused on increasing the bending flexibility of the device while maintaining good torquability. However, as described below, improved cut patterns have now been designed that increase bending flexibility of the device while optimizing pushability (i.e., optimizing axial stiffness).

Although the improved cut patterns sacrifice some of the torquability of conventional cut patterns, the enhanced pushability of the device and the improved axial stiffness to bending stiffness ratios provide more effective overall functionality, particularly in applications where axial stiffness is likely to be more important that torquability, such as in many catheter applications. For example, unlike guidewires, catheters lack a solid core and therefore inherently lack good axial stiffness. Since catheters are often routed over guidewires, the guidewires may be utilized for sub-selecting vessels and reaching the anatomical target. Thus, pushability is often more important than torquability in catheters.

The length of the catheter 10 may vary according to the needs of a particular application, but will typically be within a range of about 125 cm to 175 cm. The microfabricated portion will likely vary according to particular application needs, but will typically have a length of about 50 to 90 cm. The distal-most sections (e.g., the distal-most section is about 10 to 30 cm) typically have a higher degree of microfabrication so as to be more flexible. As with catheter length, catheter diameter may vary according to application needs. Examples may range from about 2 F to 10 F, though sizes outside this range may also be utilized where suitable (e.g., outside of typical neuro and coronary applications). Aspiration catheters for use in neurovascular procedures is one exemplary application for the high push strength devices described herein.

The microfabricated section of the catheter 10 includes a plurality of cuts that extend transverse to the longitudinal axis of the catheter to form "rings" and "beams." The rings are the circumferentially extending, ring-shaped structures and the beams are the uncut, axially extending sections of the tube that connect adjacent rings. Sections of the catheter 10 may be defined herein according to the number of beams disposed between each successive pair of rings.

Figure 2A:
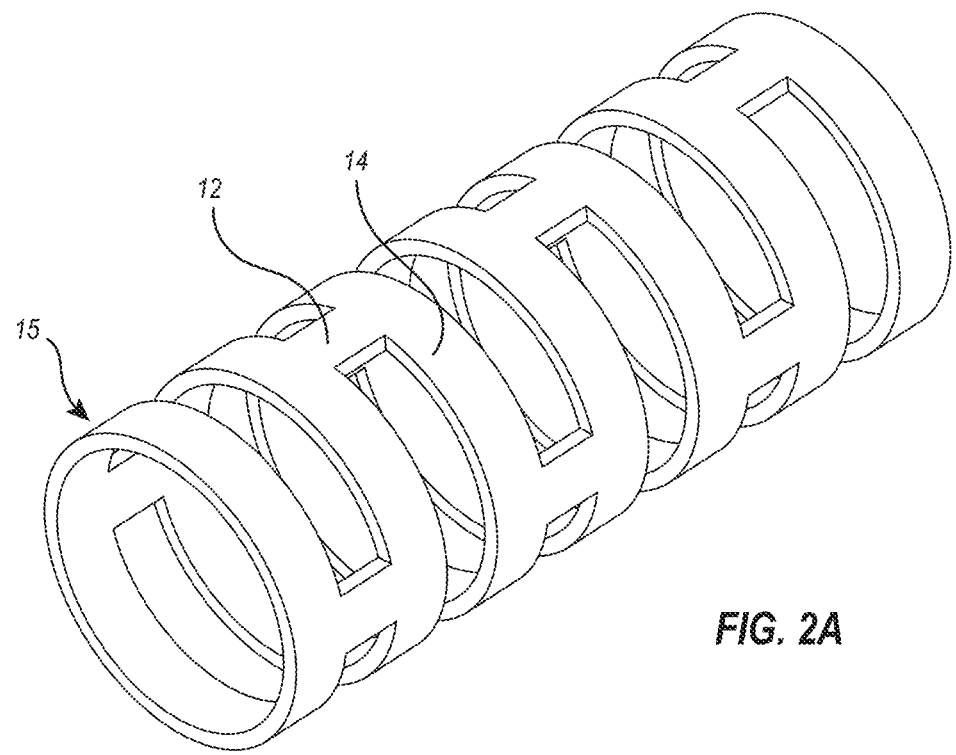
FIG. 2A is a detailed view of a microfabricated distal section of a catheter having a conventional two-beam cut pattern.
Figure 2B:
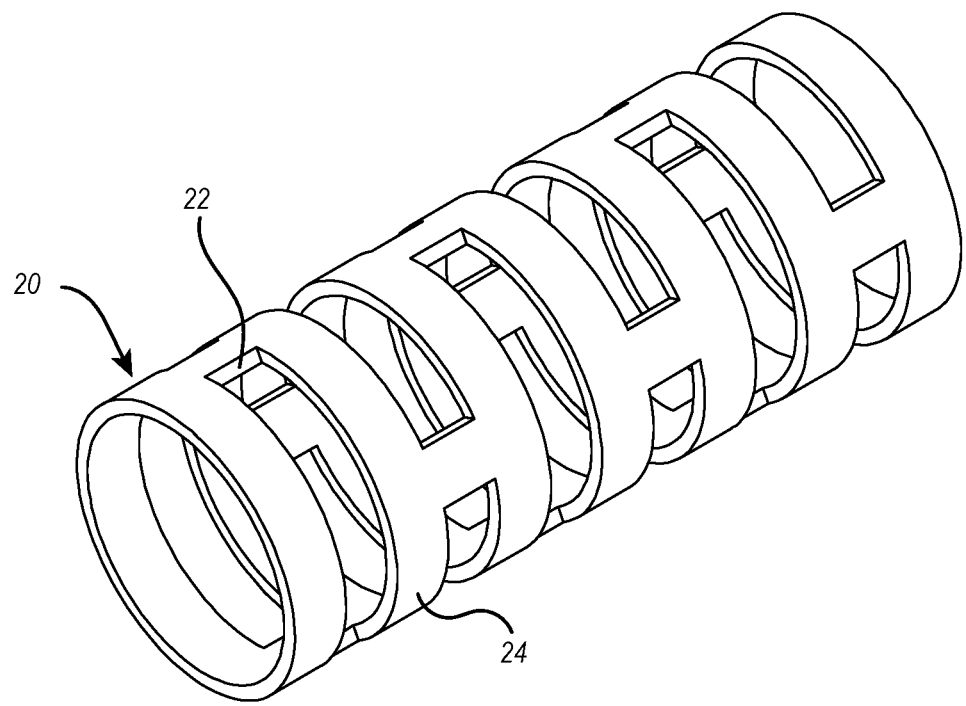
FIGS. 2B and 2C are detailed views of microfabricated distal sections of catheters having three-beam and one-beam cut patterns, respectively.
Figure 2C:
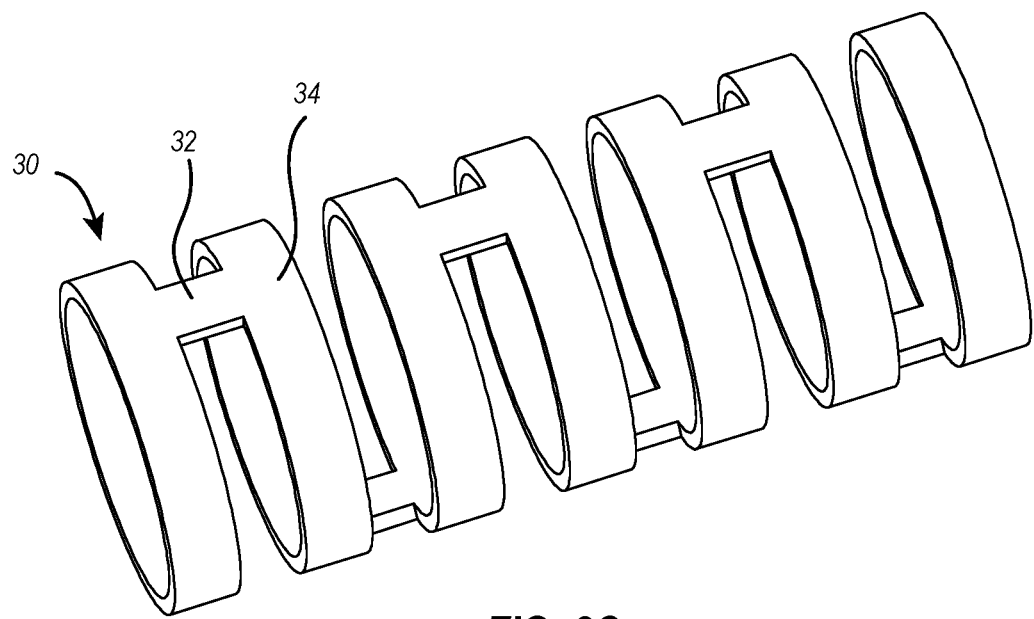

FIGS. 2A-2C illustrate conventional microfabricated configurations in order to describe general features and to define general terms. The improved features, described further below, may be applied to any of the conventional configurations shown in FIGS. 2A-2C.

FIG. 2A, for example, represents a conventional "two-beam section" 15 of a microfabricated tube member. The two-beam section includes a series of successive rings 14 and a series of beams 12 extending between and connecting the rings. As shown, each pair of adjacent rings 14 is connected by two beams 12. FIG. 2B illustrates a "three-beam section" 20 with where three of the beams 22 are disposed between each set of adjacent rings 24. FIG. 2C illustrates a "one-beam section" 30 where a single beam 32 extends between and connects each pair of adjacent rings 34. Although most of the examples described herein will reference the two-beam configuration, it will be understood that the same features may be applied to other embodiments having one-beam or three-beam configurations, or even to configurations having other numbers of beams between each set of adjacent rings.

Figure 3A:
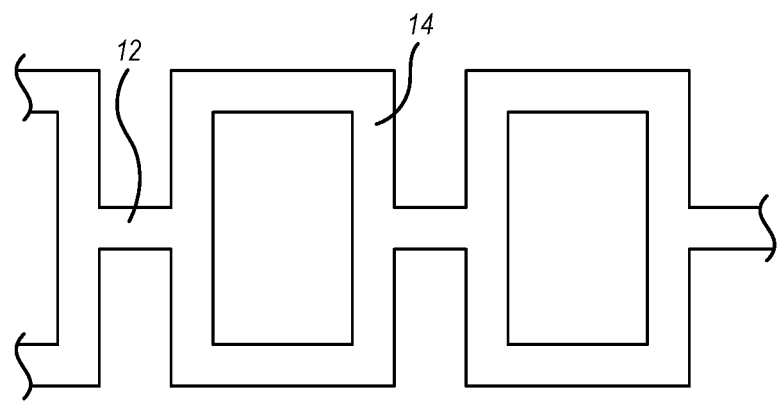
FIGS. 3A and 3B schematically illustrate how microfabricated catheter sections can compress and "accordion" under an axial load.
Figure 3B:
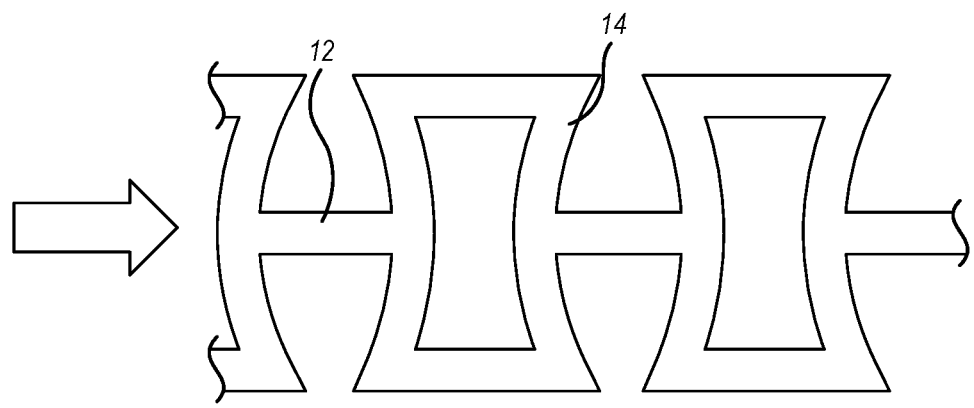

FIGS. 3A and 3B schematically illustrate how microfabricated catheter sections can compress and "accordion" under an axial load. FIG. 3A shows a side view of a conventional two-beam section (as in FIG. 2A) with beams 12 and rings 14. FIG. 3B shows that when an axial load (i.e., a push) is applied, the rings 14 may flex somewhat and absorb part of the axial load rather than fully transferring it to more distal sections of the device. This reduces the pushability of the device and makes it more difficult for the operator to track the catheter over a guidewire and/or get the catheter to the desired anatomical target.

Figure 4:
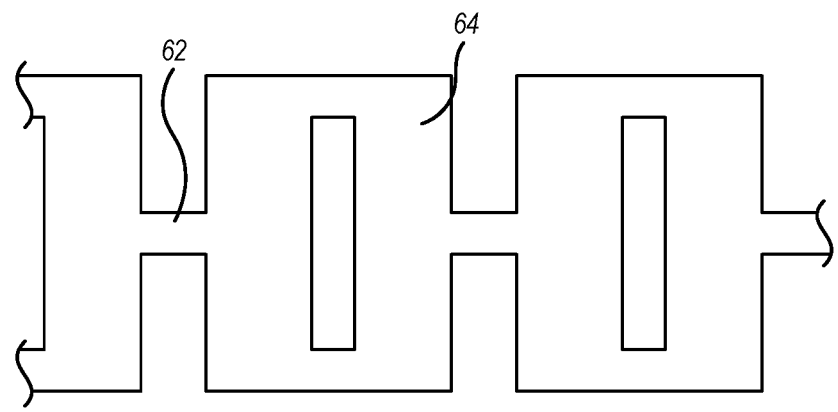
FIG. 4 illustrates a microfabricated catheter section having relatively thick ring elements to enhance axial stiffness, but which concentrate bending forces in the axial beam elements.

One way to increase the axial stiffness of the device is to simply increase the length of the rings along the axial direction (sometimes this dimension is also referred to as the "thickness," "axial length," or "width" of the rings). FIG. 4 illustrates an embodiment with increased axial length of rings 64. While increasing the axial length of rings 64 can indeed increase the axial stiffness of the device, there is a practical limit to how much the axial length of the rings 64 can be increased. For example, if the axial length of the rings 64 is increased too much relative to the size of the beams 62, excessive bending stresses will be concentrated at the beams 62. At some point, the device will be unable to bend sufficiently without plastically deforming at the beams 62. Simply increasing the ring size until a desired axial stiffness is achieved is therefore not a practical option.

High Push Strength Microfabricated Sections

FIGS. 5A and 5B illustrate an embodiment of a high push strength cut pattern that may be applied to a tube member and utilized in a catheter device such as the device shown in FIG. 1. The cut pattern beneficially provides effective axial stiffness while still maintaining good bending flexibility. Further, unlike simply expanding the thickness of the rings, the illustrated configuration allows for high relative axial stiffness without overly concentrating stresses in the beams. FIG. 5A shows an exemplary tube member 100 (e.g., a distal section of a catheter) and FIG. 5B shows the same cut pattern if the tube member 100 were cut in half along the longitudinal axis and unrolled so as to lay flat.

As shown, the elongate tube member 100 includes a series of circumferentially extending rings 114 connected together by a series of axially extending beams 112. The rings 114 have a length "L" in the axial direction. This dimension may occasionally be referred to as the ring "width," "axial length," or ring "thickness," but is typically referred to herein as the length (or more specifically the axial length) for the sake of consistency since it is the dimension parallel to the longitudinal axis of the tube member 100. Regarding the beams 112, the "length" of the beams 112 will be used herein to refer to the dimension along the axial direction, while the "width" or "thickness" of the beams will be used herein to refer to the dimension along the circumference of the tube member 100.

The rings 114 are spaced apart by transverse cuts 118 that each extend in a direction transverse to the longitudinal axis of the tube member 100 but that do not extend completely through the tube member 100. The tube member 100 is therefore somewhat similar to the conventional configurations illustrated in FIGS. 2A-2C. The illustrated tube member 100 represents a two-beam section because it includes two beams 112 between each pair of adjacent rings 114. As explained above, however, other embodiments may include configurations with a different number of beams between each pair of adjacent rings (e.g., one-beam or three-beam configurations).

Unlike the conventional configurations shown in FIGS. 2A-2C, however, the illustrated embodiment also includes a series of axial cuts 116 aligned with the beams 112. Each axial cut 116 starts along an edge of a corresponding beam 112 and extends partially into the adjoining ring 114 in a substantially axial direction so that the corresponding beam 112 is partially "nested" within the axial length of the adjoining beam 112.

The beams 112 of the illustrated embodiment in FIGS. 5A and 5B are each associated with axial cuts 116 that extend into each of the adjoining rings 114, which represents a preferred embodiment. However, other embodiments may include fewer axial cuts 116. For example, some embodiments may have beams that are only associated with axial cuts extending into one of the two adjoining rings (e.g., just the proximal adjoining ring, or just the distal adjoining ring, but not both). In another embodiment, the tube member 100 may have some beams 112 that are associated with axial cuts 116 while other of beams 112 are not associated with axial cuts 116.

Because part of the beam 112 is nested within the axial length of the ring 114, the result is a more flexible beam structure per unit length of the tube member 100 as compared to the same structure without the axial cuts 116. In other words, the illustrated cut pattern provides additional functional length to the beams 112, and thus greater bending flexibility to the device, while still allowing the rings 114 to be relatively thick (i.e., to have relatively long axial length) along most of the circumference of the device. The overall structure is therefore capable of providing good axial stiffness without overly increasing the bending stiffness, resulting in devices that have a favorable axial stiffness to bending stiffness ratio.

As shown in FIGS. 5A and 5B, the transverse cuts 118 may have a wedge-shape. The wedge-shaped cuts 118 beneficially provide additional clearance allowing the device to bend along an inside of a curve. Similarly, for embodiments that fill the gaps of the device with a polymer material, such as discussed further below, the wedge-shaped cuts 118 provide additional room for the polymer that gets compressed toward the inside of a curve.

For example, at a given axial position of the tube member 100, the transverse cuts 118 may be narrower near the beams 112 and then widen while extending away from the beams 112. Starting from one of the beams 112 and extending around the circumference, the cuts 118 can widen until reaching an apex 119 and can then begin to narrow again while continuing to extend toward the opposite beam 112. As shown, the apex 119 may be located at a location equidistant from the two beams 112, though in other embodiments one or more transverse cuts 118 may be asymmetrical and the apex 119 need not be equidistant from each beam 112.

The size and shape of the wedge-shaped transverse cuts 118 may be varied. In general, wider gaps provide greater clearance for tighter bending but at the cost of a reduction in axial stiffness. Accordingly, the wedge angle and/or gap size may be increased for applications requiring greater bending flexibility, or the wedge angle and/or gap size may be reduced for applications requiring greater axial stiffness. Alternatively, the wedge angle and/or gap may be increased for areas of the device requiring greater flexibility and reduced for areas of the device requiring greater axial strength. In one nonlimiting example, the wedge angle and/or gap size may be increased at more distal sections of the device relative to more proximal sections of the device. In certain embodiments, at least at a distal section of the tube member 100, the gap size of the apex 119 (i.e., the widest part of the transverse cut 118) may be about 25% to about 100% the length of the rings 114, or about 35% to about 75% the length of the rings 114. Additionally, or alternatively, the wedge angle may increase or decrease progressively between one section to another such that there is a gradual change in wedge angle from a first section to a second section.

The angle "A" at which the wedge-shape of the transverse cuts 118 extends from the beam 112 may range from about 2 degrees to about 35 degrees, or about 5 degrees to about 25 degrees, or about 10 degrees to about 20 degrees. In other words, if an angle of 0 degrees represents a straight, perpendicular cut, the wedge-shaped cuts 118 preferably have an angle greater than 0 degrees but less than about 35 degrees, more typically less than about 25 degrees or less than about 20 degrees.

In the illustrated embodiment, the transverse cuts 118 angle in both axial directions (proximally and distally). That is, starting at a given beam 112, and moving in a circumferentially perpendicular direction around the tube member 100 toward another beam 112, the corresponding transverse cut 118 is angled away from perpendicular along both the proximally adjoining ring 114 and the distally adjoining ring 114 Other embodiments may include transverse cuts 118 that are only angled away from perpendicular in one direction (i.e., along only the proximally adjoining ring or only along the distally adjoining ring).

One or more axial cuts 116 may be wedge-shaped. As shown in FIGS. 5A and 5B, the axial cuts 116 may be somewhat wider where the cuts "start" along the edge of the ring, and then narrow while extending along the axial direction farther into the adjoining ring. As with the wedge-shape of the transverse cuts 118, the wedge shape of the axial cuts 116 may provide additional clearance allowing more movement of the rings 114 relative to the beam 112 allowing the rings 114 to better bend towards one another along the inside of a curve when the tube member 100 is bent. If a straight axial cut (parallel to the longitudinal axis) has a cut angle of 0 degrees, the angle of the axial cuts 116 may be greater than 0 degrees but less than about 35 degrees, more typically less than about 25 degrees or less than about 20 degrees.

At least for distal sections of the tube member 100, the axial cuts 116 may extend into the adjoining rings 114 a distance equal to about 25% to about 75%, or about 35% to about 65%, or about 45% to about 55% of the axial length of the rings 114. The greater the axial cuts 116 extend into the rings 114, the greater the added functional length of the associated beam 112. However, this comes at the expense of some of the structure of the rings, and thus deeper axial cuts 116 reduce some of the structure of the ring 114 otherwise contributing to axial stiffness, at least at the particular portion of the ring 114 coincident with the axial cuts 116 and the beam 112. In some applications, the axial cuts 116 may extend farther into the rings 114 to increase the length of the associated beam 112 and thus the flexibility of the tube member 100. In other applications, the axial cuts 116 may extend farther into the ring 114 on one section of the device relative to another section of the device. For example, the axial cuts 116 may be increased or decreased near the distal or proximal ends of the device.

Accordingly, the beam length may also increase or decrease in size. This may be a result of the length of the axial cut 116 as discussed above. Alternatively, or in addition, the beam length may vary in size independent of the axial cut 116 by increasing or decreasing the length of the portion of the beams 112 between the corresponding pair of rings 114. In some application, one section of the tube member 100 may have a beam length which is longer relatively than the beam length of another section in order to give the device differential flexibility on different parts of the device. Finally, the beam length may vary progressively from a first section to a second section such that the beam length increases or decreases gradually between the two sections.

The beam width, or the beam thickness, may also vary in size according to the application of the device, the overall size of the device, and/or the section of the device. In some applications, one section of a device may have a beam width that is larger relatively than a second section of the device. In addition, the beam width may vary progressively such that the beam width of each beam 112 increases gradually between a first section and a second section.

The ring size may also vary according to the overall size of the device and/or the section of the device. For example, at a distal section of the tube member 100, the rings 114 may have a ring length to ring diameter ratio of about 0.25 to 0.8, or about 0.35 to 0.65, or about 0.4 to 0.6. In some applications, the entire device will have a utilize similar ring sizes with each ring 114 having similar axial length. Alternatively, in some applications, the ring size of one or more sections of the device will differ from one or more other sections of the device such that one or more sections of the device have greater axial strength relative to one or more other sections. In some embodiments, the ring axial length may vary along the device progressively, such that the ring size increases or decreases gradually from one section to another section.

As shown, the beams 112 between each pair of adjacent rings 114 may be equally circumferentially spaced (e.g., spaced by 180 degrees in a two-beam configuration), although other embodiments may arrange the beams so as not to be equally circumferentially spaced. Sets of beams 112 may also be rotationally offset from adjoining sets of beams 112. For example, a set of beams 112 between a given pair of adjacent rings may be rotationally offset from the set of beams of a previous and/or subsequent pair of adjacent rings. In the illustrated embodiment, the rotational offset is 90 degrees. That is, a first pair of beams is provided at a first rotational position, then while moving along the length of the tube member 100 the next pair of beams is offset from the first pair by 90 degrees.

Other rotational offsets may be utilized. The rotational offset may be about 5 degrees to about 90 degrees, for example. A rotational offset that is less than 90 degrees provides a helical pattern that minimizes preferred bending axes in the tube member 100. Other beneficial "distributed" beam arrangements may alternatively be utilized to avoid preferred bending axes. These are described in more detail in U.S. patent application Ser. No. 16/616,139, entitled "Micro-Fabricated Medical Device Having a Non-Helical Cut Arrangement," which is incorporated herein by this reference in its entirety.

The tube member 100 may be formed from any material or combination of materials suitable for an intravascular application. Examples include polymer materials such as polyether ether ketone (PEEK), other polymers that can be formulated with a similar range for modulus of elasticity, stainless steel, or superelastic materials such as nitinol. Preferred embodiments are formed from nitinol.

As briefly mentioned above, a polymer material may be added to the tube member 100 to fill in the gaps made by transverse cuts 118 and axial cuts 116 and allow the tube member 100 to be transport fluids. The polymer material may comprise an elastomer such as a polyether block amide and/or another similar polymer.

Another advantage of the described embodiments as compared to the conventional configurations relates to the relatively lower open gap space along the outer surface of the tube member 100. Because the improved cut patterns allow for increased axial length of the rings, less of the overall outer surface area is taken up by gaps. This means that proportionally less of the device relies on the polymer material for maintaining fluid tight integrity under pressure and thus the device is less likely to fail when delivering fluids under pressure.

Other embodiments may omit a polymer material. For example, certain applications may not require the delivery or aspiration of fluids and can feasibly utilize a device where the gaps are not filled. Keeping the gaps open is beneficial, in certain applications, because adding polymer to the transverse and axial cuts increases the bending stiffness of the tube member 100. Other embodiments may utilize one or more liners rather than a polymer fill material. For example, an inner liner may be disposed along an inner surface of the tube member 100 and/or an outer liner may be disposed along an outer surface of the tube member 100. Either way, the inner liner and the outer liner do not fill the gaps of the tube member 100. Such embodiments may advantageously keep the gaps of the transverse and axial cuts open and unobstructed, which reduces the amount of resistance to bending and thereby allows for lower bending stiffness.

It should be understood that the foregoing features are primarily directed toward a distal section of the tube member 100. Similar features may be utilized in more proximal sections. However, more proximal sections typically do not require the same bending flexibility and so such sections may be tailored more toward pushability and/or torquability and less toward bending flexibility. Thus, more proximal sections may be modified via one or more of increasing the axial lengths of the rings, increasing the width of the beams, decreasing the size of the wedge-shaped gaps, decreasing the depth of the axial cuts, or increasing the number of beams between each pair of rings.

EXAMPLES

A useful metric for comparing intravascular devices is the ratio of axial stiffness to bending stiffness. Axial stiffness and bending stiffness (i.e., flexural rigidity) are typically reported using different units. In the SI system, for example, axial stiffness is typically reported in units of force per distance (e.g., Newtons per meter), while bending stiffness is typically reported in units of force times distance squared (e.g., Newtons times meters squared). When using such units, a useful metric can be determined by comparing the ratio of the axial stiffness to the bending stiffness of a micromachined structure and comparing that number to the ratio of axial stiffness to bending stiffness of a homogenous material (not micromachined but otherwise similar to the micromachined structure). For example, the ratio of axial stiffness to bending stiffness of the micromachined structure can be divided by the ratio of axial stiffness to bending stiffness of the homogenous material to provide a useful comparative ratio illustrating how the micromachined structure compares to a baseline homogenous material. Such an overall ratio is unitless. This metric is referred to herein as the micromachined-to-homogenous ratio.

A variety of catheter devices and materials were tested to measure ratios of axial stiffness to bending stiffness. Materials tested included tubes of homogenous rubber and plastic materials, including PEBAX® (a polyether block amide), polyurethane, and the like. Commercial catheter devices formed with sections of coil and/or braided material were also tested. The micromachined-to-homogenous ratio for commercially available catheters typically ranged from about 1 to 2.5. The highest micromachined-to-homogenous ratios were found in certain commercial catheter products with coil and/or braided sections and were measured to be about 3.

In comparison with the above, tube members formed with a high push strength configuration as shown in FIG. 5A were also tested. Tube members formed from nitinol were the most preferred, though tube members formed of other materials also performed well. The high push strength configuration provided micromachined-to-homogenous ratios that were significantly higher than those for common coil and/or braid arrangements. Tube members with the high push strength configuration had micromachined-to-homogenous ratios greater than 3, and in some instances much greater than 3. Certain tests showed micromachined-to-homogenous ratios of about 14. Certain tests even showed micromachined-to-homogenous ratios of up to 100 at distal sections of the tube having high degrees of microfabrication.

Additional Terms & Definitions

While certain embodiments of the present disclosure have been described in detail, with reference to specific configurations, parameters, components, elements, etcetera, the descriptions are illustrative and are not to be construed as limiting the scope of the claimed invention.

Furthermore, it should be understood that for any given element of component of a described embodiment, any of the possible alternatives listed for that element or component may generally be used individually or in combination with one another, unless implicitly or explicitly stated otherwise.

In addition, unless otherwise indicated, numbers expressing quantities, constituents, distances, or other measurements used in the specification and claims are to be understood as optionally being modified by the term "about" or its synonyms. When the terms "about," "approximately," "substantially," or the like are used in conjunction with a stated amount, value, or condition, it may be taken to mean an amount, value or condition that deviates by less than 20%, less than 10%, less than 5%, or less than 1% of the stated amount, value, or condition. At the very least, and not as an attempt to limit the application of the doctrine of equivalents to the scope of the claims, each numerical parameter should be construed in light of the number of reported significant digits and by applying ordinary rounding techniques.

Any headings and subheadings used herein are for organizational purposes only and are not meant to be used to limit the scope of the description or the claims.

It will also be noted that, as used in this specification and the appended claims, the singular forms "a," "an" and "the" do not exclude plural referents unless the context clearly dictates otherwise. Thus, for example, an embodiment referencing a singular referent (e.g., "widget") may also include two or more such referents.

It will also be appreciated that embodiments described herein may include properties, features (e.g., ingredients, components, members, elements, parts, and/or portions) described in other embodiments described herein. Accordingly, the various features of a given embodiment can be combined with and/or incorporated into other embodiments of the present disclosure. Thus, disclosure of certain features relative to a specific embodiment of the present disclosure should not be construed as limiting application or inclusion of said features to the specific embodiment. Rather, it will be appreciated that other embodiments can also include such features.

The invention claimed is:

1. A microfabricated, elongate tube member for an intravascular device, the elongate tube member extending along a longitudinal axis and comprising:
   a plurality of circumferentially extending rings, each ring having an axial length;
   a plurality of transverse cuts each positioned between adjacent rings, each transverse cut extending in a direction transverse to the longitudinal axis of the tube member;
   a plurality of axially extending beams each extending from one ring to another to connect adjacent rings; and
   a plurality of wedge-shaped axial cuts, the plurality of wedge-shaped axial cuts including
      (i) proximal cuts that, for each beam, begin at an edge of an adjoining proximal ring and extend partially into the adjoining proximal ring in a substantially proximal axial direction so that the beam is at least partially nested within the length of the adjoining proximal ring, wherein each proximal cut is widest where it begins at the edge of the adjoining proximal ring and progressively narrows while extending along the proximal axial direction into the adjoining proximal ring, and
      (ii) distal cuts that, for each beam, begin at an edge of an adjoining distal ring and extend partially into the adjoining distal ring in a substantially distal axial direction so that the beam is at least partially nested within the length of the adjoining distal ring, wherein each distal cut is widest where it begins at the edge of the adjoining distal ring and progressively narrows while extending along the distal axial direction into the adjoining distal ring;
   wherein the proximal cuts and/or distal cuts of the plurality of wedge-shaped axial cuts extend further into the ring on a first section of the elongate tube member relative to a second section of the elongate tube member;
   wherein the first section of the elongate tube member is positioned proximally or distally of the second section; and
   wherein the first section of the elongate tube member has a flexibility different than a flexibility of the second section of the elongate tube member.

2. The tube member of claim 1, wherein at least a portion of the transverse cuts are wedge-shaped.

3. The tube member of claim 2, wherein at least a portion of the transverse cuts are narrower near the corresponding beams and widen while circumferentially extending away from the corresponding beams.

4. The tube member of claim 1, wherein the tube member has a two-beam configuration such that there is a pair of beams between each pair of adjacent rings, and the pair of beams between each pair of adjacent rings are circumferentially spaced by about 180 degrees.

5. The tube member of claim 4, wherein the two-beam configuration includes a rotational offset such that the beams between a given pair of adjacent rings are rotationally offset from beams of a previous and/or subsequent pair of adjacent rings.

6. The tube member of claim 5, wherein the rotational offset is about 5 degrees to about 90 degrees.

7. The tube member of claim 1, wherein a ring axial length progressively decreases toward a distal end of the tube member.

8. The tube member of claim 1, wherein beam thickness progressively decreases toward a distal end of the tube member.

9. The tube member of claim 1, wherein at a distal section of the tube member, the rings have a ring length to ring diameter ratio of about 0.25 to 0.8.

10. The tube member of claim 1, wherein at least a section of the tube member has a micromachined-to-homogenous ratio of at least 3.

11. The tube member of claim 1, wherein the tube member is formed from one or more of polyether ether ketone (PEEK), stainless steel, or nitinol.

12. The tube member of claim 1, further comprising a polymer applied to the tube member to fill in the transverse cuts and the axial cuts.

13. The tube member of claim 1, further comprising one or both of an inner liner or an outer liner.

14. The tube member of claim 13, wherein the one or both of an inner liner or an outer liner do not fill in the transverse cuts or the axial cuts.

15. The tube member of claim 1, wherein the beam length increases or decreases from a first section of the tube member to a second section of the tube member.

16. The tube member of claim 1, wherein the beams are arranged so as not to be equally circumferentially spaced.

17. A microfabricated, elongate tube member for an intravascular device, the elongate tube member extending along a longitudinal axis and comprising:
   a plurality of circumferentially extending rings, each ring having an axial length;
   a plurality of axially extending beams each extending from one ring to another to connect adjacent rings; and
   a plurality of wedge-shaped axial cuts, the plurality of wedge-shaped axial cuts including
     (i) proximal cuts that, for each beam, begin at an edge of an adjoining proximal ring and extend partially into the adjoining proximal ring in a substantially proximal axial direction so that the beam is at least partially nested within the length of the adjoining proximal ring, wherein each proximal cut is widest where it begins at the edge of the adjoining proximal ring and progressively narrows while extending along the proximal axial direction into the adjoining proximal ring, without widening again, and
     (ii) distal cuts that, for each beam, begin at an edge of an adjoining distal ring and extend partially into the adjoining distal ring in a substantially distal axial direction so that the beam is at least partially nested within the length of the adjoining distal ring, wherein each distal cut is widest where it begins at the edge of the adjoining distal ring and progressively narrows while extending along the distal axial direction into the adjoining distal ring without widening again;
   wherein the proximal cuts and distal cuts of the plurality of wedge-shaped axial cuts extend further into the ring on a first section of the elongate tube member relative to a second section of the elongate tube member;
   wherein the first section of the elongate tube member is positioned distally of the second section;
   wherein within the first section and/or the second section the proximal and distal cuts extend to the same respective distance;
   wherein the first section of the elongate tube member has a flexibility different than a flexibility of the second section of the elongate tube member, and
   wherein any section of elongate tube member distal of the first section does not have proximal and/or distal cuts that extend into a ring to a depth that is less than the depth of the proximal and distal cuts of the first section.

18. The tube member of claim 17, wherein at least a portion of the wedge-shaped axial cuts form a wedge angle that is greater than 0 degrees and up to approximately 35 degrees.

19. The tube member of claim 18, wherein the wedge angle increases or decreases along the tube member.

* * * * *